United States Patent
Stein et al.

(10) Patent No.: US 9,328,347 B2
(45) Date of Patent: May 3, 2016

(54) SIRNA USEFUL IN THE TREATMENT OF FLAVIVIRUS INFECTION

(75) Inventors: David A. Stein, Corvallis, OR (US); Klaus Frueh, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 88 days.

(21) Appl. No.: 14/233,494

(22) PCT Filed: Jul. 17, 2012

(86) PCT No.: PCT/US2012/047000
§ 371 (c)(1),
(2), (4) Date: May 16, 2014

(87) PCT Pub. No.: WO2013/012835
PCT Pub. Date: Jan. 24, 2013

(65) Prior Publication Data
US 2014/0248336 A1    Sep. 4, 2014

Related U.S. Application Data

(60) Provisional application No. 61/509,002, filed on Jul. 18, 2011.

(51) Int. Cl.
*C12N 15/11* (2006.01)
*C12N 15/113* (2010.01)

(52) U.S. Cl.
CPC ........ *C12N 15/1131* (2013.01); *C12N 2310/14* (2013.01); *C12N 2320/11* (2013.01); *C12N 2770/24111* (2013.01)

(58) Field of Classification Search
USPC ......... 435/6.1, 91.1, 91.31, 455, 458; 514/44; 536/23.1, 24.5; 424/450
See application file for complete search history.

(56) References Cited

U.S. PATENT DOCUMENTS

| 2002/0155435 A1* | 10/2002 | Wang ................... C07K 14/005 435/5 |
| 2003/0092684 A1* | 5/2003 | Fredeking .............. A61K 35/14 514/152 |
| 2005/0159379 A1* | 7/2005 | McSwiggen ... C12Y 103/01022 514/44 A |
| 2007/0167393 A1 | 7/2007 | McSwiggen |
| 2009/0047338 A1 | 2/2009 | Swamy |
| 2010/0254945 A1 | 10/2010 | Ge |

\* cited by examiner

*Primary Examiner* — Jane Zara
(74) *Attorney, Agent, or Firm* — Jeffrey M. Jackson

(57) ABSTRACT

Pharmaceutical compositions that comprise an siRNA molecule used in the treatment of diseases caused by flavivirus infection and methods of their use are disclosed. The pharmaceutical compositions treat diseases caused by yellow fever virus, West Nile virus, and dengue virus and include a single pharmaceutical composition active against all four dengue virus serotypes.

33 Claims, 12 Drawing Sheets

Figure 2A

Figure 2B

Figure 5A uucaauaugcugaaacgcgagagaaa gucaauaugcuaaaacgcggaaugcc

Figure 5B

Figure 5C

SEQUENCE LISTING

<160> NUMBER OF SEQ ID NOS: 21

<210> SEQ ID NO 1
<211> LENGTH: 19
<212> TYPE: RNA
<213> ORGANISM: Artificial Sequence
<220> FEATURE:
<223> OTHER INFORMATION: siRNA

<400> SEQUENCE: 1
acgugacguu cggagaauu                                              19

<210> SEQ ID NO 2
<211> LENGTH: 19

```
<212> TYPE: RNA
<213> ORGANISM: Dengue virus

<400> SEQUENCE: 2
gggcaauggu ugugggcua                                                   19

<210> SEQ ID NO 3
<211> LENGTH: 19
<212> TYPE: RNA
<213> ORGANISM: Dengue virus

<400> SEQUENCE: 3
ggauggagcu ugagagaaa                                                   19

<210> SEQ ID NO 4
<211> LENGTH: 19
<212> TYPE: RNA
<213> ORGANISM: Dengue virus

<400> SEQUENCE: 4
cgggaaagac gaagagaua                                                   19

<210> SEQ ID NO 5
<211> LENGTH: 19
<212> TYPE: RNA
<213> ORGANISM: Dengue virus

<400> SEQUENCE: 5
ccaaagaggu aguggacaa                                                   19

<210> SEQ ID NO 6
<211> LENGTH: 19
<212> TYPE: RNA
<213> ORGANISM: Dengue virus

<400> SEQUENCE: 6
gaggaaugcu ugugagaaa                                                   19

<210> SEQ ID NO 7
<211> LENGTH: 19
<212> TYPE: RNA
<213> ORGANISM: Dengue virus

<400> SEQUENCE: 7
ggauggagcc uuagagaaa                                                   19

<210> SEQ ID NO 8
<211> LENGTH: 19
<212> TYPE: RNA
<213> ORGANISM: Dengue virus

<400> SEQUENCE: 8
ccaaagaggu aguggacaa                                                   19

<210> SEQ ID NO 9
<211> LENGTH: 19
<212> TYPE: RNA
<213> ORGANISM: Dengue virus

<400> SEQUENCE: 9
ggauggagcu uaagagaaa                                                   19

<210> SEQ ID NO 10
```

```
<211> LENGTH: 20
<212> TYPE: RNA
<213> ORGANISM: Dengue virus

<400> SEQUENCE: 10
aguuguuagu cuacguggac                                            20

<210> SEQ ID NO 11
<211> LENGTH: 19
<212> TYPE: RNA
<213> ORGANISM: Dengue virus

<400> SEQUENCE: 11
auuagagagc agaucucug                                             19

<210> SEQ ID NO 12
<211> LENGTH: 19
<212> TYPE: RNA
<213> ORGANISM: Dengue virus

<400> SEQUENCE: 12
ugcugaaacg cgagagaaa                                             19

<210> SEQ ID NO 13
<211> LENGTH: 19
<212> TYPE: RNA
<213> ORGANISM: Dengue virus

<400> SEQUENCE: 13
gguuagagga gaccccucc                                             19

<210> SEQ ID NO 14
<211> LENGTH: 19
<212> TYPE: RNA
<213> ORGANISM: Dengue virus

<400> SEQUENCE: 14
ggacuagagg uuagaggag                                             19

<210> SEQ ID NO 15
<211> LENGTH: 19
<212> TYPE: RNA
<213> ORGANISM: Dengue virus

<400> SEQUENCE: 15
aacagcauau ugacgcugg                                             19

<210> SEQ ID NO 16
<211> LENGTH: 19
<212> TYPE: RNA
<213> ORGANISM: Dengue virus

<400> SEQUENCE: 16
ccagagaucc ugcugucuc                                             19

<210> SEQ ID NO 17
<211> LENGTH: 19
<212> TYPE: RNA
<213> ORGANISM: West Nile virus

<400> SEQUENCE: 17
gucaauaguc uaaaacgcg                                             19
```

```
<210> SEQ ID NO 18
<211> LENGTH: 19
<212> TYPE: RNA
<213> ORGANISM: Yellow fever virus

<400> SEQUENCE: 18
cccugggcgu caauauggu                                                        19

<210> SEQ ID NO 19
<211> LENGTH: 19
<212> TYPE: RNA
<213> ORGANISM: Dengue virus

<400> SEQUENCE: 19
uuucucucgc guuucagca                                                        19

<210> SEQ ID NO 20
<211> LENGTH: 19
<212> TYPE: RNA
<213> ORGANISM: West Nile virus

<400> SEQUENCE: 20
cgcguuuuag acuauugac                                                        19

<210> SEQ ID NO 21
<211> LENGTH: 19
<212> TYPE: RNA
<213> ORGANISM: Yellow fever virus

<400> SEQUENCE: 21
accauauuga cgcccaggg                                                        19
```

SIRNA USEFUL IN THE TREATMENT OF FLAVIVIRUS INFECTION

FIELD

Figure 1A:
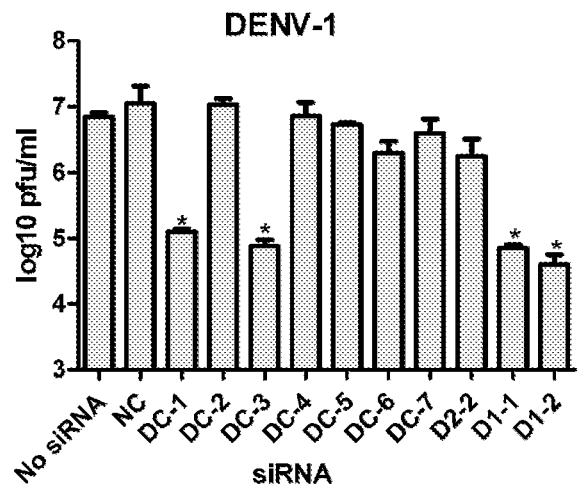
Figure 1B:
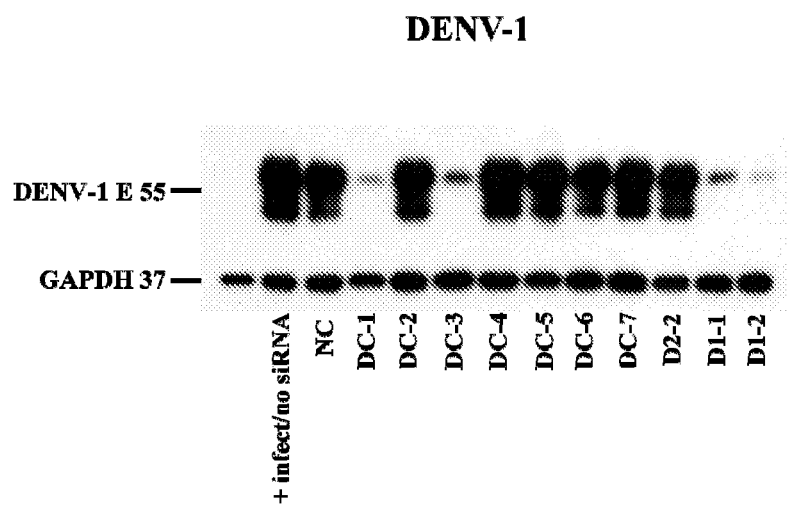

This disclosure relates to the field of treatment of viral infections and specifically to siRNA compositions and methods of their use in the prevention and treatment of diseases caused by flavivirus infections.

BACKGROUND

More than one-third of the world's population lives in areas at risk for transmission of dengue virus (DENV). Dengue virus is a flavivirus, in the same genus as West Nile virus and Yellow Fever virus. Dengue virus is a leading cause of illness in the tropics and subtropics, with as many as 100 million people infected yearly. Dengue is caused by any one of four related viral serotypes (DENV-1, DENV-2, DENV-3, and DENV-4) transmitted by mosquitoes. It is critical that once dengue infection is detected, that prompt supportive treatment be administered. Infection may be asymptomatic or it may cause a spectrum of clinical syndromes ranging from self-limiting febrile illness to life-threatening severe dengue disease. Hundreds of thousands of clinical dengue disease cases are reported by clinicians annually to the WHO and dengue disease has a mortality rate of 0.5% to 5.0%. Any of the four serotypes can cause severe disease in humans and all four serotypes circulate globally. (Guy B and Almond J W, *Comp Immunol Microbiol Infect Dis* 31, 239-252 (2008); Guzman M G et al, *Nat Rev Microbiol* 8 S7-S16 (2010); Halstead S B, *Lancet* 370, 1644-1652 (2007); and Wilder-Smith et al *Curr Infect Dis Rep* 12, 157-164 (2011); all of which are incorporated by reference in their entireties.)

SUMMARY

DENV genomic sequences can vary by up to 10% between strains within a serotype and can vary up to 35% between different serotypes. (Guzman et al 2010; Weaver S C and Vasilakis N, *Infect Genet Evol* 9, 523-540 (2009), hereby incorporated by reference in its entirety). This sequence variability makes development of both vaccines and compositions for the treatment of dengue very difficult. Because treatment of dengue disease must occur very rapidly after symptoms develop, a composition used in the treatment of dengue disease must work against all four serotypes of dengue. A pharmaceutical composition that works against less than all serotypes would not be a fully effective therapeutic because it could require a serotype identification test prior to treatment. A serotype identification would delay treatment at best and could be unavailable in areas in which dengue is endemic. Similarly, a pharmaceutical composition that works against fewer than all serotypes would be ineffective as a prophylactic treatment due to the fact that all four serotypes circulate throughout the world.

Currently, there is no approved vaccine for DENV or any approved antiviral composition to treat DENV either prophylactically or therapeutically that is available to clinicians, and no approved single agent that has demonstrated efficacy against infection by all four DENV serotypes.

There is an urgent need for pharmaceutical compositions useful in treating flaviviruses, especially a single pharmaceutical composition that is capable of treating all four serotypes of the dengue virus. It is disclosed herein that a pharmaceutical composition comprising a siRNA that includes a sequence of any of SEQ ID NOs: 2-19 is capable of treating one or more flavivirus infections. More specifically, a pharmaceutical composition that comprises a siRNA that comprises a nucleic acid that comprises SEQ ID NO: 12 or SEQ ID NO: 19 is capable of treating all four serotypes, (DENV-1, DENV-2, DENV-3, and DENV-4) of dengue.

Disclosed herein are pharmaceutical compositions that may be used in the treatment of a flavivirus infection. In one embodiment, the pharmaceutical compositions comprise a siRNA and a pharmaceutically acceptable carrier configured to deliver the siRNA to a cell susceptible to infection with a flavivirus. The siRNA comprises a nucleic acid, the nucleic acid comprising one or more of the following sequences: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The siRNA may further comprise a second nucleic acid. The second nucleic acid comprises the complement of the first nucleic acid. The first nucleic acid and the second nucleic acid form a nucleotide duplex. The first and second nucleic acids may be linked to one another by a first linker in order to form a hairpin secondary structure. Alternatively, the first and second nucleic acids that are linked by a first linker may also be linked by a second linker in order to form a circular single-stranded polynucleotide. In one example, the first nucleic acid comprises SEQ ID NO: 12 and the second nucleic acid comprises SEQ ID NO: 19.

The siRNA may be of any length, including equal to or less than 27 nucleotides in length. Either strand of the siRNA may further comprise an overhang such as a 5'- or 3'-overhang. The overhang may be of any length, including 1-4 nucleotides in length.

The siRNA may comprise one or more modified nucleotides. A modified nucleotide may be any appropriate modification of the siRNA, such as a locked nucleic acid nucleotide, a G-clamp nucleotide, a nucleotide base analog, or a nitroazole derivative. The siRNA may comprise a terminal cap moiety or a phosphate backbone modification or a conjugate attached to the siRNA via a linker.

The pharmaceutically acceptable carrier may be any system that delivers the siRNA such as a lipid based, polymer based, cyclodextrin based or protein based carrier system. Alternatively, the carrier may be naked siRNA.

The flavivirus may be any flavivirus, such as dengue virus, West Nile virus, or yellow fever virus. If the flavivirus is dengue virus, then the dengue virus may be of any serotype including DENV-1, DENV-2, DENV-3, or DENV-4.

Disclosed herein are methods of treating a flavivirus infection in a subject. In one embodiment, the method involves administering a pharmaceutical composition to a subject, the pharmaceutical composition comprising an siRNA, the siRNA comprising a sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, and SEQ ID NO: 19.

The subject may be any subject, including a human being. The subject may display signs or symptoms of flavivirus infection and where the pharmaceutical composition is administered therapeutically. Alternatively, the subject may display no signs or symptoms of flavivirus infection, but is present in or will be present in a region in which a flavivirus is endemic and where the pharmaceutical composition is administered prophylactically.

The pharmaceutical composition may be administered by any route, including injection, oral administration, sublingual administration, rectal administration, transdermal administration, intranasal administration, vaginal administration, retro-orbital administration, and through inhalation. If the pharmaceutical composition is administered by injection, the injection may be through any injection mode including subcutaneous injection, intramuscular injection, intradermal injection, intraperitoneal injection, or intravenous injection.

One example of a pharmaceutical composition can be administered to the patient is one that comprises a nucleotide that includes SEQ ID NO: 12 and another nucleotide that includes SEQ ID NO: 19. The flavivirus being treated may be any flavivirus. If the flavivirus is dengue virus, then the dengue virus may be of any serotype including DENV-1, DENV-2, DENV-3, or DENV-4. If the subject shows symptoms of dengue disease, but the serotype of the dengue infection is not known, then the subject may be treated with the pharmaceutical composition described in the example.

BRIEF DESCRIPTION OF THE DRAWINGS

FIG. 1A is a bar graph showing the effects of in vitro treatment with the listed siRNA on DENV-1 viral titer by plaque forming assay.

FIG. 1B is an image showing the effects of in vitro treatment with the listed siRNA upon DENV-1 viral titer by Western blot.

FIG. 1C is a bar graph showing the effects of in vitro treatment with the listed siRNA on DENV-2 viral titer by plaque forming assay.

FIG. 1D is an image showing the effects of in vitro treatment with the listed siRNA upon DENV-2 viral titer by Western blot.

FIG. 1E is a bar graph showing the effects of in vitro treatment with the listed siRNA on DENV-3 viral titer by plaque forming assay.

FIG. 1F is an image showing the effects of in vitro treatment with the listed siRNA upon DENV-3 viral titer by Western blot.

FIG. 1G is a bar graph showing the effects of in vitro treatment with the listed siRNA on DENV-4 viral titer by plaque forming assay.

FIG. 1H is an image showing the effects of in vitro treatment with the listed siRNA upon DENV-4 viral titer by Western blot.

FIG. 2A is a bar graph showing the percentage of DENV strains in GenBank having a 0 or 1 base mismatch in the regions targeted by the listed siRNA.

FIG. 2B is a bar graph showing the percentage of DENV strains having a 0 or 1 base mismatch in the regions targeted by the listed siRNA separated by DENV serotype.

FIG. 3A is a line graph showing the effects of in vitro treatment with an siRNA that includes SEQ ID NO: 12 on DENV-1 viral titer over time.

FIG. 3B is a line graph showing the effects of in vitro treatment with an siRNA that includes SEQ ID NO: 12 on DENV-2 viral titer over time.

FIG. 3C is a line graph showing the effects of in vitro treatment with an siRNA that includes SEQ ID NO: 12 siRNA on DENV-3 viral titer over time.

FIG. 3D is a line graph showing the effects of in vitro treatment with an siRNA that includes SEQ ID NO: 12 siRNA on DENV-4 viral titer over time.

FIG. 4A is a line graph showing the effects of in vitro treatment with different amounts of an siRNA that includes SEQ ID NO: 12 siRNA on DENV-2 viral titer.

FIG. 4B is a line graph showing the effects of in vitro treatment with different amounts of an siRNA that includes SEQ ID NO: 5 on DENV-2 viral titer.

FIG. 5A is an alignment of the 5'CS regions of DENV-2 (top), bases 131-158 and WNV (bottom), bases 136-161.

FIG. 5B is a bar graph showing the effects of an siRNA comprising SEQ ID NO: 17 on WNV titer.

FIG. 5C is a bar graph showing the effects of an siRNA comprising SEQ ID NO: 18 on YFV titer.

FIG. 6A is a survival curve showing the effects of the indicated siRNA on animal survival in a mouse model of DENV disease.

FIG. 6B is a line graph showing the effects of the indicated siRNA on animal weight in a mouse model of DENV disease.

FIG. 6C shows the effects of an siRNA that includes SEQ ID NO: 12 on DENV-2 titer in serum and spleen in a mouse model of DENV disease 24 and 72 hours after infection FIG. 6D shows the effects of an siRNA that includes SEQ ID NO: 12 on DENV-2 titer in liver, kidney and small intestine in a mouse model of DENV disease 72 hours after infection.

FIG. 6E shows the effects of an siRNA that includes SEQ ID NO: 12 on serum TNF-$\alpha$ in a mouse model of DENV disease 24 and 72 hours after infection.

SEQUENCE LISTING

SEQ ID NO: 1 is an irrelevant sequence used as a negative control for siRNA compositions.

SEQ ID NO: 2 is the sense strand of a siRNA that targets the location in DENV-1 indicated in Table 1.

SEQ ID NO: 3 is the sense strand of a siRNA that targets the location in DENV-1 indicated in Table 1.

SEQ ID NO: 4 is the sense strand of a siRNA that targets the location in DENV-2 indicated in Table 1.

SEQ ID NO: 5 is the sense strand of a siRNA that targets the location in DENV-2 indicated in Table 1.

SEQ ID NO: 6 is the sense strand of a siRNA that targets the location in DENV-3 indicated in Table 1.

SEQ ID NO: 7 is the sense strand of a siRNA that targets the location in DENV-3 indicated in Table 1.

SEQ ID NO: 8 is the sense strand of a siRNA that targets the location in DENV-4 indicated in Table 1.

SEQ ID NO: 9 is the sense strand of a siRNA that targets the location in DENV-3 indicated in Table 1.

SEQ ID NO: 10 is the sense strand of a siRNA that targets the location indicated in Table 1 that is conserved across all four DENV serotypes.

SEQ ID NO: 11 is the sense strand of a siRNA that targets the location indicated in Table 1 that is conserved across all four DENV serotypes.

SEQ ID NO: 12 is the sense strand of a siRNA that targets the location indicated in Table 1 that is conserved across all four DENV serotypes.

SEQ ID NO: 13 is the sense strand of a siRNA that targets the location indicated in Table 1 that is conserved across all four DENV serotypes.

SEQ ID NO: 14 is the sense strand of a siRNA that targets the location indicated in Table 1 that is conserved across all four DENV serotypes.

SEQ ID NO: 15 is the sense strand of a siRNA that targets the location indicated in Table 1 that is conserved across all four DENV serotypes.

SEQ ID NO: 16 is the sense strand of a siRNA that targets the location indicated in Table 1 that is conserved across all four DENV serotypes.

SEQ ID NO: 17 is the sense strand of a siRNA that targets the location in WNV indicated in Table 1.

SEQ ID NO: 18 is the sense strand of a siRNA that targets the location in YFV indicated in Table 1.

SEQ ID NO: 19 is the antisense strand of a siRNA that targets the same location as that of SEQ ID NO: 12 and that is the complement of SEQ ID NO: 12.

DETAILED DESCRIPTION

Disclosed herein includes sequences of siRNA molecules useful in the prophylactic or therapeutic treatment of flavivirus infection. Flaviviruses that may be treated using the disclosed siRNA molecules include any of the dengue virus serotypes (DENV-1, DENV-2, DENV-3, and DENV-4), West Nile virus, and yellow fever virus.

siRNA Compositions:

Disclosed herein are compositions that comprise interfering RNA molecules, particularly siRNA molecules capable of silencing flavivirus gene expression through an RNAi mechanism. In particular, these compositions include one or more of the sense sequences listed in Table 1 and/or any complementary sequences thereof.

Interfering RNA (which may be interchangeably referred to as RNAi or an interfering RNA sequence refers to double-stranded RNA that is capable of silencing, reducing, or inhibiting expression of a target gene by any mechanism of action now known or yet to be disclosed. For example, RNAi may act by mediating the degradation of mRNAs which are complementary to the sequence of the RNAi when the RNAi is in the same cell as the target gene. RNAi thus refers to both the double-stranded RNA formed by two complementary RNA strands or by a single, self-complementary strand. RNAi may have substantial or complete identity to the target gene or may comprise one or more mismatches upon alignment to the target gene. The sequence of the interfering RNA may correspond to the full length target gene, or any subsequence thereof.

The concept of RNAi includes small-interfering RNA, which may interchangeably be referred to as siRNA. An siRNA may be any interfering RNA with a duplex length of about 15-60, 15-50, or 15-40 nucleotides in length, more typically about 15-30, 15-25, or 18-23 nucleotides in length. Each complementary sequence of the double-stranded siRNA may be 15-60, 15-50, 15-40, 15-30, 15-25, or 18-23 nucleotides in length, but other noncomplementary sequences may be present. For example, siRNA duplexes may comprise 3' overhangs of 1 to 4 or more nucleotides and/or 5' phosphate termini comprising 1 to 4 or more nucleotides. A siRNA may be synthesized in any of a number of conformations. One skilled in the art would recognize the type of siRNA conformation to be used for a particular purpose. Examples of siRNA conformations include, but need not be limited to, a double-stranded polynucleotide molecule assembled from two separate stranded molecules, wherein one strand is the sense strand and the other is the complementary antisense strand; a double-stranded polynucleotide molecule assembled from a single-stranded molecule, where the sense and antisense regions are linked by a nucleic acid-based or non-nucleic acid-based linker; a double-stranded polynucleotide molecule with a hairpin secondary structure having complementary sense and antisense regions; or a circular single-stranded polynucleotide molecule with two or more loop structures and a stem having self-complementary sense and antisense regions. In the case of the circular polynucleotide, the polynucleotide may be processed either in vivo or in vitro to generate an active double-stranded siRNA molecule.

The siRNA can be chemically synthesized, may be encoded by a plasmid and transcribed, or may be vectored by a virus engineered to express the siRNA. A siRNA may be a single stranded molecule with complementary sequences that self-hybridize into duplexes with hairpin loops. siRNA can also be generated by cleavage of parent dsRNA through the use of an appropriate enzyme such as *E. coli* RNase III or Dicer (Yang et al, *Proc. Natl. Acad. Sci. USA* 99, 9942-9947 (2002); Calegari et al, *Proc. Natl. Acad. Sci. USA* 99, 14236-14240 (2002); Byrom et al, *Ambion TechNotes* 10, 4-6 (2003); Kawasaki et al, *Nucleic Acids Res* 31, 981-987 (2003); Knight et al, *Science* 293, 2269-2271 (2001); and Robertson et al, *J Biol Chem* 243, 82-91 (1968)). A parent dsRNA may be any double stranded RNA duplex from which an siRNA may be produced, such as a full or partial mRNA transcript.

A mismatch motif may be any portion of a siRNA sequence that is not 100% complementary to its target sequence. A siRNA may have zero, one, two, or three or more mismatch regions. The mismatch regions may be contiguous or may be separated by any number of complementary nucleotides. The mismatch motifs or regions may comprise a single nucleotide or may comprise two or more consecutive nucleotides.

A siRNA molecule may be capable of inhibiting the expression of a target gene, such as a flavivirus gene or an entire flaviviral genome. The terms "silencing" or "reducing" may be used interchangeably with "inhibiting." To examine the extent of inhibition of expression by a siRNA, a siRNA of interest is added to a test sample and to a negative control sample to which the siRNA was not added. Preferably, a negative control sample is similar to the test sample. More preferably, the negative control sample is identical to the test sample. Examples of negative control samples include untreated samples, samples to which a siRNA-free buffer was added, or samples to which a negative control or mock siRNA (such as SEQ ID NO: 1) was added. Expression in the test sample is then compared to expression in the negative control sample. Expression may be measured by the detection of any expression product known in the art or yet to be disclosed. Typical expression products that may be detected include RNA, protein, or whole virus.

Methods known in the art for the detection and quantification of RNA expression in a sample include northern blotting and in situ hybridization (Parker and Barnes, *Methods in Molecular Biology* 106, 247-283 (1999); RNAse protection assays (Hod, *Biotechniques* 13, 852-854 (1992)); and PCR-based methods, such as reverse transcription polymerase chain reaction (RT-PCR) (Weis et al., *Trends in Genetics* 8, 263-264 (1992)). Representative methods for sequencing-based gene expression analysis include Serial Analysis of Gene Expression (SAGE), and gene expression analysis by massively parallel signature sequencing (MPSS). (See Mardis E R, *Annu Rev Genomics Hum Genet* 9, 387-402 (2008)).

For example: proteins can be detected and quantified through epitopes recognized by polyclonal and/or monoclonal antibodies used in methods such as ELISA, immunoblot assays, flow cytometric assays, immunohistochemical assays, radioimmuno assays, Western blot assays, an immunofluorescent assays, chemiluminescent assays and other polypeptide detection strategies. Proteins may also be detected by mass spectrometry assays (potentially coupled to immunoaffinity assays) including matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS). Additionally, protein expression may be detected by tagging of proteins separated by two-dimensional polyacrylamide gel electrophoresis (2D-PAGE), (Kiernan et al, *Anal Biochem* 301, 49-56 (2002); Poutanen et al, *Mass Spectrom* 15, 1685-1692 (2001)) or any other method of detecting protein.

Whole viral expression or viral titer may be performed through any method of detecting viral RNA or protein such as those listed above, or through a plaque forming assay.

In general, negative control samples are assigned a value of 100%. Inhibition of expression of a target gene may be achieved when the expression of the test sample relative to the control sample is 95%, 90%, 85%, 80%, 75%, 70%, 65%, 60%, 55%, 50%, 45%, 40%, 35%, 30%, 25%, 20%, 15%, 10%, 5%, 1%, less than 1% or 0%. Expression of a test sample relative to a negative control sample may also be presented in terms of fold reduction, such as a 2-fold, 3-fold, 5-fold, 10-fold, 20-fold, 50-fold, 100-fold or more than 100 fold less expression than the negative control sample.

Two or more nucleic acid sequences or subsequences may be referred to as being substantially identical, meaning that they are exactly the same or have a specified percentage of nucleotides that are the same. Substantially identical nucleotides may have at least 60%, 65%, 70%, 75%, 80%, 85%, 90%, 95%, or more than 95% identity over a specified region when compared and aligned for maximum correspondence. This definition, when the context indicates, also refers to the complement of a sequence. Preferably, the substantial identity exists over a region that is at least about 5, 10, 15, 20, 25, 30, 35, 40, 45, 50, 55, or 60 nucleotides in length.

SiRNA molecules can be provided in several forms including, e.g., as one or more isolated siRNA duplexes, as longer double-stranded RNA (dsRNA), or as siRNA or dsRNA transcribed from a transcriptional cassette in a DNA plasmid. The siRNA sequences may have overhangs (as 3' or 5' overhangs as described in Elbashir et al, *Genes Dev* 15, 188 (2001) or Nykänen et al, *Cell* 107, 309 (2001)) or may lack overhangs (i.e., have blunt ends).

One or more DNA plasmids encoding one or more siRNA templates may be used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (Brummelkamp et al, *Science* 296, 550 (2002); Donzé et al, *Nucleic Acids Res* 30, e46 (2002); Paddison et al, *Genes Dev* 16, 948 (2002); Yu et al, *Proc Natl Acad Sci USA* 99, 6047 (2002); Lee et al, *Nat Biotech*, 20, 500 (2002); Miyagishi et al, *Nat Biotech* 20, 497 (2002); Paul et al, *Nat Biotech*, 20, 505 (2002); and Sui et al, *Proc Natl Acad Sci USA,* 99, 5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al (2002) supra). The selected promoter can provide for constitutive or inducible transcription. Compositions and methods for DNA-directed transcription of RNA interference molecules are described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a nucleic acid to a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler and Hoffman, *Gene* 25, 263-269 (1983); Sambrook and Russell, *Molecular Cloning: A Laboratory Manual*, Cold Spring Harbor Laboratory Press, Cold Spring Harbor N.Y., (2001)) as are PCR methods (see, U.S. Pat. Nos. 4,683,195 and 4,683, 202; *PCR Protocols: A Guide to Methods and Applications*, Innis et al, eds, (1990)). Expression libraries are also well known to those of skill in the art. Additional basic texts disclosing the general methods of use in this invention include Sambrook and Russell (2001) supra; Kriegler, *Gene Transfer and Expression: A Laboratory Manual* (1990); and *Current Protocols in Molecular Biology* (Ausubel et al., eds., 1994).

A siRNA molecule may be chemically synthesized. In one example of chemical synthesis, a single-stranded nucleic acid that includes the siRNA duplex sequence can be synthesized using any of a variety of techniques known in the art, such as those described in Usman et al, *J Am Chem Soc,* 109, 7845 (1987); Scaringe et al, *Nucl Acids Res,* 18, 5433 (1990); Wincott et al, *Nucl Acids Res,* 23, 2677-2684 (1995); and Wincott et al, *Methods Mol Bio* 74, 59 (1997). Synthesis of the single-stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 micromolar scale protocol with a 2.5 min coupling step for 2'-O-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the siRNA single-stranded molecules, methods for RNA deprotection, and methods for RNA purification are known to those of skill in the art.

A siRNA can also be synthesized via a tandem synthesis technique, wherein both strands are synthesized as a single continuous fragment or strand separated by a linker that is subsequently cleaved to provide separate fragments or strands that hybridize to form an siRNA duplex. The linker may be any linker, including a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, the siRNA can be assembled from two distinct single-stranded molecules, wherein one strand includes the sense strand and the other includes the antisense strand of the siRNA. For example, each strand can be synthesized separately and joined together by hybridization or ligation following synthesis and/or deprotection. Either the sense or the antisense strand may contain additional nucleotides that are not complementary to one another and do not form a double stranded siRNA. In certain other instances, the siRNA molecules can be synthesized as a single continuous fragment, where the self-complementary sense and antisense regions hybridize to form a siRNA duplex having hairpin secondary structure.

A siRNA molecule may comprise a duplex having two complementary strands that form a double-stranded region with least one modified nucleotide in the double-stranded region. The modified nucleotide may be on one strand or both. If the modified nucleotide is present on both strands, it may be in the same or different positions on each strand. A modified siRNA may be less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in the art, for example in Saenger, *Principles of Nucleic Acid Structure*, Springer-Verlag Ed. (1984), are also suitable for use in siRNA molecules. Other modified nucleotides include, without limitation: locked nucleic acid (LNA) nucleotides, G-clamp nucleotides, or nucleotide base analogs. LNA nucleotides include but need not be limited to 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc,* 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res,* 29, 2437-2447 (2001)).

A siRNA molecule may comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3 aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al, *Tetrahedron* 49, 1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al, *Modern Synthetic Methods*, VCH, 331-417 (1995); Mesmaeker et al, *Antisense Research*, ACS, 24-39 (1994)). Such chemical modifications can occur at the 5'-end and/or 3'-end of the sense strand, antisense strand, or both strands of the siRNA.

The sense and/or antisense strand of a siRNA may comprise a 3'-terminal overhang having 1 to 4 or more 2'-deoxyribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626 and 20050282188.

A siRNA molecule may comprise one or more non-nucleotides in one or both strands of the siRNA. A non-nucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the siRNA may also comprise attaching a conjugate to the siRNA molecule. The conjugate can be attached at the 5'- and/or the 3'-end of the sense and/or the antisense strand of the siRNA via a covalent attachment such as a nucleic acid or non-nucleic acid linker. The conjugate can also be attached to the siRNA through a carbamate group or other linking group (see, e.g., U.S. Patent Publication Nos. 20050074771, 20050043219, and 20050158727). A conjugate may be added to the siRNA for any of a number of purposes. For example, the conjugate may be a molecular entity that facilitates the delivery of the siRNA into a cell or the conjugate a molecule that comprises a drug or label. Examples of conjugate molecules suitable for attachment to the siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the siRNA can be evaluated for improved pharmacokinetic profiles, bioavailability, and/or stability of the siRNA while retaining activity. As such, one skilled in the art can screen siRNA molecules having various conjugates attached thereto to identify siRNA conjugates having improved properties using any of a variety of well-known in vitro cell culture or in vivo animal models.

A siRNA may be incorporated into a carrier systems containing the siRNA molecules described herein. The carrier system may be a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex (see US Patent Application Publication 20070218122). In further embodiments, the carrier system is a protein-based carrier system such as a cationic peptide-nucleic acid complex. A siRNA molecule may also be delivered as naked siRNA.

Flaviviruses

Disclosed herein are compositions useful in the treatment of infection with a flavivirus, including dengue virus, West Nile virus (WNV), and yellow fever virus (YFV) and methods of use thereof. Flaviviruses are small, enveloped viruses containing a single, positive-strand, genomic RNA, approximately 10,500 nucleotides in length containing short 5' and 3' non-translated regions (NTRs), a single long open reading frame, a 5' cap, and a nonpolyadenylated 3' terminus. Examples of flaviviruses include all four dengue serotypes (DENV-1, DENV-2, DENV-3, and DENV-4) yellow fever virus, Japanese encephalitis virus, West Nile virus and tick-borne encephalitis virus and others. Flaviviral proteins are derived from a single polypeptide processed by host and viral proteases. The gene products encoded by the single open reading frame include capsid (C), preMembrane (prM, which is processed to Membrane (M) just prior to virion release from the cell), Envelope (E) and the non-structural (NS) proteins.

The dengue virus species comprises a variety of genetically distinct strains within four antigenically distinguishable serotypes known as DENV-1, DENV-2, DENV-3, and DENV-4. Dengue is a member of the genus Flavivirus in the family Flaviviridae (Calisher C H et al, *J Gen Virol* 70 (Pt1), 37-43 (1989); Rico-Hesse R, *Virology* 174, 479-493 (1990); and Weaver S C and Vasilakis N, *Infect Genet Evol* 9, 523-540 (2009); all of which are hereby incorporated by reference in their entireties.) Symptoms of DENV infection by any serotype may include but need not be limited to high fever, headache, aching muscles and joints, rash, severe hemorrhage, vascular permeability, shock, or any combination of these. The more severe form of dengue disease may be termed dengue hemorrhagic fever/dengue shock syndrome.

Treatment of Flavivirus Infection:

Disclosed herein include methods of treating a subject that has or may have a flavivirus infection comprising administering a pharmaceutical composition comprising an siRNA molecule capable of inhibiting a flavivirus infection to the subject. The subject may be treated therapeutically or prophylactically.

A subject may be any multi-cellular vertebrate organisms, a category that includes human and non-human mammals, such as mice. In some examples a subject is a male. In some examples a subject is a female. Further types of subjects to which the pharmaceutical composition may be properly administered include subjects known to have a flavivirus infection (through, for example, a molecular diagnostic test or clinical diagnosis) subjects having a predisposition to contracting a flavivirus infection (for example by travel to a region in which a flavivirus is endemic), or subjects displaying one or more symptoms of having a flavivirus infection.

Administration of an agent may be any method of providing or give a subject an agent, such as an siRNA capable of treating flavivirus infection, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Treating a subject may be any therapeutic intervention that ameliorates a sign or symptom of a disease or pathological condition after it has begun to develop, whether or not the subject has developed symptoms of the disease. Ameliorating, with reference to a disease, pathological condition or symptom refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the memory and/or cognitive function of the subject, a qualitative improvement in symptoms observed by a clinician or reported by a patient, or by other parameters well known in the art that are specific to flavivirus infection.

A symptom may be any subjective evidence of disease or of a subject's condition, for example, such evidence as perceived by the subject; a noticeable change in a subject's condition indicative of some bodily or mental state. A sign may be any abnormality indicative of disease, discoverable on examination or assessment of a subject. A sign is generally an objective indication of disease.

A pharmaceutical composition may be any chemical compound or composition capable of inducing a desired therapeutic or prophylactic effect when properly administered to a subject. A pharmaceutical composition can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent is an agent that significantly reduces one or more symptoms associated with flavivirus infection. A pharmaceutical composition may be a member of a group of compounds. Pharmaceutical compositions may be grouped by any characteristic including chemical structure and the molecular target they affect.

The administration of treatments for flavivirus infection can be for either prophylactic or therapeutic purposes. When provided prophylactically, the treatments for flavivirus infection are provided in advance of any clinical symptom of flavivirus infection. Prophylactic administration serves to prevent or ameliorate any subsequent disease process. When provided therapeutically, the compounds are provided at (or shortly after) the onset of a symptom of disease. For prophylactic and therapeutic purposes, the treatments for flavivirus infection can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the treatments for flavivirus infection can be provided as repeated doses within a prolonged prophylaxis or treatment regimen that will yield clinically significant results to alleviate one or more symptoms or detectable conditions associated with flavivirus infection.

A pharmaceutically acceptable carrier (interchangeably termed a vehicle) may be any material or molecular entity that facilitates the administration or other delivery of the pharmaceutical composition. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows trafficking of a siRNA to the spleen, blood, liver, or kidney, or one that allows the siRNA to be taken up by a flavivirus infected cell.

A therapeutically effective amount or concentration may be any amount of a composition that alone, or together with one or more additional therapeutic agents is sufficient to achieve a desired effect in a subject, or in a cell being treated with the agent. The effective amount of the agent will be dependent on several factors, including, but not limited to, the subject or cells being treated and the manner of administration of the therapeutic composition. In one example, a therapeutically effective amount or concentration is one that is sufficient to prevent advancement, delay progression, or to cause regression of a disease, or which is capable of reducing symptoms caused by any disease, including flavivirus infection.

In one example, a desired response is to reduce or inhibit one or more symptoms associated with flavivirus infection. The one or more symptoms do not have to be completely eliminated for the composition to be effective. For example, a composition can decrease the sign or symptom by a desired amount, for example by at least 20%, at least 50%, at least 80%, at least 90%, at least 95%, at least 98%, or even at least 100%, as compared to the sign or symptom in the absence of the composition. A therapeutically effective amount of a disclosed pharmaceutical composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 100 µg-10 mg per kg body weight if administered intravenously. The actual dosages of treatments for flavivirus infection will vary according to factors such as the type of flavivirus to be protected against (for example, DENV-1, DENV-2, DENV-3, DENV-4, WNV, or YFV) and the particular status of the subject (for example, the subject's age, size, fitness, extent of symptoms, susceptibility factors, and the like), time and route of administration, other drugs or treatments being administered concurrently, as well as the specific pharmacology of treatments for flavivirus infection for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount of treatments for flavivirus infection within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight to about 10 mg/kg body weight per dose.

Dosage can be varied by the attending clinician to maintain a desired concentration. Higher or lower concentrations can be selected based on the mode of delivery, for example, transepidermal, rectal, oral, pulmonary, intranasal delivery, intravenous or subcutaneous delivery.

Determination of effective dosages is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, viral titer assays or cell culture infection assays). Using such models, only ordinary calculations and adjustments are required to determine an appropriate concentration and dose to administer a therapeutically effective amount of the treatments for flavivirus infection (for example, amounts that are effective to alleviate one or more symptoms of flavivirus infection).

Suitable methods, materials, and examples used in the practice and/or testing of embodiments of the disclosed invention are described below. Such methods and materials are illustrative only and are not intended to be limiting. Other methods, materials, and examples similar or equivalent to those described herein can be used.

EXAMPLES

Example 1

Methods

Cells.

Huh7 cells (a human hepatoma derived cell line) and Vero cells were propagated in a growth medium comprising Dulbecco's modification of Eagle's medium (DMEM), 10% heat inactivated fetal bovine serum (FBS), penicillin (100 unit/ml) and streptomycin (100 g/ml). Cells were cultured at 37° C. in a humidified atmosphere with 5% $CO_2$. The DENV-1 strain used was West-Pac, GenBank Accession Number DVU88535. The DENV-2 strain used was New Guinea C, GenBank Accession Number AF038403. The DENV-3 strain used was H87, GenBank Accession Number M93130. The DENV-4 strain used was H241, GenBank Accession Number AY947539. The West Nile Virus strain used was 385-99, GenBank Accession Number AY842931. 385-99 is described in Xiao S Y et al, *Emerg Infect Dis* 7, 714-721 (2001) which is incorporated by reference in its entirety.

Viruses.

Viral stocks were prepared and titered as described in Shum D et al, *Assay Drug Dev Technol* 8, 553-570 (2010) which is hereby incorporated by reference in its entirety. The WHO Primary Seed Lot 213/77 yellow fever virus 17D Passage 237, GenBank Accession Number NC_002031 was propagated on Vero cells. DENV-2 strain S221, a triple-plaque-purified clone isolated from mouse-passaged DENV-2 strain D2S10 was prepared and quantified as described in Shresta S et al, *J Virol* 80, 10208-10217 (2006), which is hereby incorporated by reference in its entirety.

siRNA Design and Bioinformatics.

The Dharmacon algorithm (Dharmacon siRNA Design Center, www.dharmacon.com, Birmingham A et al, *Nat Protoc* 2, 2068-2078, (2007); Reynolds A et al, *Nat Biotechnol* 22, 326-330 (2004), all of which are hereby incorporated by reference in their entireties) was used to design siRNA optimized to target the individual genomes of each of the four DENV serotypes used in these examples. Use of the algorithm resulted in a list of sequences ranked according to their likelihood to represent an effective siRNA target. The analysis was performed on each of the four Dengue serotypes. Two overlapping, high scoring sequences per DENV strain were selected from the lists.

TABLE 1

Names, sequences, target locations of siRNA.

| Name | Sequence | Viral Target | Location in Viral Genome[1,2,3] | SEQ ID NO: |
|---|---|---|---|---|
| NC | ACGUGACGUUCGGAGAAUU | N/A | N/A (negative control) | 1 |
| D1-1 | GGGCAAUGGUUGUGGGCUA | DENV-1 | 1237-1255 (E) | 2 |
| D1-2 | GGAUGGAGCUUGAGAGAAA | DENV-1 | 9803-9821 (NS5) | 3 |
| D2-1 | CGGGAAAGACGAAGAGAUA | DENV-2 | 5111-5129 (NS3) | 4 |
| D2-2 | CCAAAGAGGUAGUGGACAA | DENV-2 | 9360-9378 (NS5) | 5 |
| D3-1 | GAGGAAUGCUUGUGAGAAA | DENV-3 | 8096-8114 (NS5) | 6 |
| D3-2 | GGAUGGAGCCUUAGAGAAA | DENV-3 | 9727-9745 (NS5) | 7 |
| D4-1 | CCAAAGAGGUAGUGGACAA | DENV-4 | 9353-9371 (NS5) | 8 |
| D4-2 | GGAUGGAGCUUAAGAGAAA | DENV-4 | 9798-9816 (NS5) | 9 |
| DC-1 | AGUUGUUAGUCUACGUGGAC | DENV 1-4 | 1-20 (5'-UTR) | 10 |
| DC-2 | AUUAGAGAGCAGAUCUCUG | DENV 1-4 | 78-96 (5'-UTR) | 11 |
| DC-3 | UGCUGAAACGCGAGAGAAA | DENV 1-4 | 140-158 (C) | 12 |
| DC-4 | GGUUAGAGGAGACCCCUCC | DENV 1-4 | 10501-10519 (3'-UTR) | 13 |
| DC-5 | GGACUAGAGGUUAGAGGAG | DENV 1-4 | 10580-10598 (3'-UTR) | 14 |
| DC-6 | AACAGCAUAUUGACGCUGG | DENV 1-4 | 10616-10634 (3'-UTR) | 15 |
| DC-7 | CCAGAGAUCCUGCUGUCUC | DENV 1-4 | 10641-10659 (3'-UTR) | 16 |
| WNV-1 | GUCAAUAGUCUAAAACGCG | WNV | 136-154(C) | 17 |
| YFV-1 | CCCUGGGCGUCAAUAUGGU | YFV | 147-165(C) | 18 |
| DC-3 anti | UUUCUCUCGCGUUUCAGCA | DENV 1-4 | 140-158(C) complimentary to SEQ ID NO: 12 | 19 |
| WNV-1- anti | CGCGUUUUAGACUAUUGAC | WNV | 136-154 (C) complimentary to SEQ ID NO: 17 | 20 |

TABLE 1-continued

Names, sequences, target locations of siRNA.

| Name | Sequence | Viral Target | Location in Viral Genome[1,2,3] | SEQ ID NO: |
|---|---|---|---|---|
| YFV-1 Anti | ACCAUAUUGACGCCCAGGG | YFV | 147-165 (C) Compliemtary to SEQ ID NO: 18 | 21 |

[1]based on GenBank Accessions DENV1, NC_001477; DENV-2 NC_001474; DENV-3 NC_001475; DENV-4 NC_002640; WNV DQ211652; YFV NC)002031
[2]genome region containing target shown in parentheses.
[3]for SEQ ID NOs 10-16, 19, the target nucleotide position numbers correspond to DENV-2 NC_001474.

The sequences resulting from the use of the algorithm (serotype-siRNA) are SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9.

Additional siRNA sequences were designed to target sequences that are highly conserved among the four main DENV serotypes. Full length genomic sequences for the NCBI reference strains of the four DENV serotypes were aligned using TCoffee (www.tcoffee.org). This analysis resulted in six regions of 19 contiguous nucleotides with a 0 to 1 base difference between the four reference strains. The sequences of these regions are SEQ ID NO: 11, SEQ ID NO: 12, SEQ ID NO: 13, SEQ ID NO: 14, SEQ ID NO: 15, and SEQ ID NO: 16. A 20-nucleotide region having perfect conservation between the GenBank reference sequences for DENV-1, DENV-2, and DENV-3, but 2 mismatches with DENV-4 was also selected as a target sequence (SEQ ID NO: 10). Eight sequences (SEQ ID NOs: 10-16 and SEQ ID NO: 5) were aligned with a library of 2754 full-length DENV genomes deposited in GenBank. Serotype representation of the 2754 full-length DENV genomes is depicted in Table 2.

TABLE 2

Number of DENV isolate genomes in Genbank per serotype.

| Serotype | Number of Genomes in GenBank |
|---|---|
| DENV-1 | 223 |
| DENV-2 | 1852 |
| DENV-3 | 587 |
| DENV-4 | 92 |

NCBI BLAST blastn was used to align each of SEQ ID NOs: 10-16 and SEQ ID NO: 5 against all of the genomes in the library. Settings were as follows: Results reported=3000, gap opening penalty=2, gap extension penalty=1, nucleotide mismatch penalty=−1, nucleotide match reward=+1, e-value cutoff=10.0. Multiple alignments for any query/genome pair were eliminated and only the top alignment was considered. Exact matches were defined as BLAST alignments of the full length of the query (all 20 nucleotides of SEQ ID NO: 10 and all 19 nucleotides of SEQ ID NOs: 5, 10-16) with 100% identities. Single mismatches were defined as BLAST alignments of length of query −1 (19 nucleotides of SEQ ID NO: 10 and 18 nucleotides of SEQ ID NOs: 5, 10-16). with 100% identities or full-length alignments with 1 mismatch.

WNV and YFV sequences (SEQ ID NO: 17, and SEQ ID NO: 18) were compared to libraries of WNV and YFV from the NCBI nt database, which has 284 complete WNV genomes and 18 complete YFV genomes using blastn. Settings were as follows: Results reported=3000, gap opening penalty=2, gap extension penalty=1, nucleotide mismatch penalty=−1, nucleotide match reward=+1, e-value cut-off=10.0.

A random sequence negative control siRNA (SEQ ID NO: 1) was prepared for the purpose of controlling for the effects of off-target effects of the siRNA chemistry. All siRNA were analyzed with blastn against all human transcript sequences and relevant siRNA against mouse transcript sequences.

siRNA Transfection of Cells.

A transfection mixture comprising 1 or 10 μM stock of siRNA and 1 μl RNAiMax® was mixed into 100 μl OPTI-MEM® for 30 minutes at room temperature. Then 3×10$^4$ Huh7 cells in a 300 μl volume of DMEM+2% FBS (without antibiotics) was added and mixed gently. After two days, the media was removed and the cells infected with virus at either 0.2 or 0.5 multiplicity of infection (MOI) in a 200 μl volume of DMEM+2% FBS+penicillin and streptomycin for 2 hours with gentle rocking. After the two hour period, the media with virus was removed. Cells were washed twice in DMEM+2% FBS+penicillin and streptomycin and replenished with 250 μl DMEM+2% FBS+penicillin and streptomycin. Times of collections of supernatants for plaque analysis are indicated in Table 3. Times are in hours post infection.

| MOI | Volume post infection | Virus | Time collected post infection |
|---|---|---|---|
| 0.5 | 250 μl | WNV | 24 hours |
| 0.5 | 250 μl | DENV | 48 hours |
| 0.5 | 250 μl | YFV | 72 hours |

Cells were lysed with 200 μl of 1×SDS buffer (50 mM Tris pH 8.0, 2% SDS, 10% glycerol) for 30 minutes and collected for immunoblotting.

Growth curve experiments were performed at an MOI of 0.2 with a post infection volume of 400 μl DMEM+2% FBS+penicillin and streptomycin. A volume of 50 μl of supernatant was collected daily for 3-5 days starting at one day post infection.

Immunoblots.

Lysed cell samples were heated to 95° C. for 5 minutes and run on a 10% SDS-PAGE gel. After the gel was run for sufficient time, the samples in the gel were transferred to a polyvinylidene difluoride (PVDF) membrane. The PVDF membrane was then blocked for 1 hour in PBST (1% phosphate buffered saline with 0.1% Tween-20)+10% instant non-fat dry milk at room temperature. After blocking, two monoclonal antibodies were added to the PBST-milk buffer. One antibody binds specifically to the Envelope (E) protein of DENV and WNV (mouse monoclonal 4G2-4-15). This antibody may be referred to as anti-E or α-E. The other antibody binds specifically to GADPH, an appropriate housekeeping gene that serves as an internal loading control. The anti-GADPH antibody used was obtained from Santa Cruz Biotechnology, catalog number SC32233. The anti-E antibody was added at a concentration of 1 μg/ml. The anti-GADPH was used at a dilution of 1:7500. Both antibodies were added directly to the blocking buffer. The membrane was incubated with antibody for two hours at room temperature. The membrane was then washed with two separate washes of PBST (without dry milk). Then a horseradish peroxidase conjugated goat anti-mouse IgG secondary antibody was diluted at 1:7500 in PBST+10% milk and added to the membrane. After a one-hour incubation with the secondary antibody at room temperature, the membrane was rinsed with PBST and detected with SuperSignal West Pico® chemiluminescent substrate (Thermo Scientific).

Titer Determination.

Viral titers for DENV and WNV were determined using Vero cells by immunostaining of foci. Such an assay used in determining viral titer may also be referred to as a plaque assay. Serial dilutions of each virus were made in DMEM+2% FBS+penicillin+streptomycin. The dilutions were then used to infect confluent monolayers of Vero cells for 90 minutes. The media containing the virus was then removed and replaced with a culture media containing DMEM+2% FBS+penicillin+streptomycin+0.5% carboxymethylcellulose sodium salt (CMC). The culture media was then removed after two days (in the case of WNV) or after four days (in the case of DENV). After removal of the culture media, cells were fixed with 4% paraformaldehyde (PFA) w/v in 1×PBS for 15 minutes prior to immunostaining.

To perform the immunostaining, the paraformaldehyde solution was removed and the cells were washed twice with 1×PBS. Cells were then blocked in 1×PBS+2% normal goat serum (NGS) and 0.4% Triton X-100. Percentages for the blocking solution are v/v. Mouse monoclonal anti-E was then diluted to 4 μg/ml in 1×PBS+2% NGS and added to the cells. The cells were incubated with the anti-E for one hour then washed twice with 1×PBS. The secondary antibody, horseradish peroxidase conjugated goat anti-mouse IgG, was diluted 1:5000 in 1×PBS with 2% NGS. This was then added to the cells and incubated for one hour. After the incubation with the secondary antibody, the cells were rinsed twice with 1×PBS. Immunoreactive foci were stained with Vector VIP® Peroxidase and pfu/ml calculated on the basis of the number of immunoreactive foci. In the case of YFV, viral titers were determined using Vero cells by plaque assay. Serial dilutions of YFV were made in DMEM+10% FBS. The dilutions were used to infect confluent monolayers of Vero cells for one hour. After infection, the monolayers were overlaid with 1% agar in double deionized water mixed in a 1:1 ratio with 2×EMEM+5% FBS+penicillin+streptomycin. Three days after the infection, an additional overlay with 0.015% (w/v) neutral red in 1% agar was added. Four days after the infection, viral plaques were counted.

Cell Viability Assay.

Uninfected Huh7 cells were subjected to the indicated treatment using the same reverse-transfection and cell culture conditions as in the antiviral assays described, except that 96 well plates (as opposed to 48 well plates) and appropriately scaled reagent volumes were used. Cells were plated at 1×10$^4$ cells per well. Cell viability was measured at 48 hours after plating using the CellTiter Glo® cell proliferation assay kit (Promega) by following the manufacturer's instructions (hereby incorporated by reference in their entirety). A Turner Biosystems plate reader was used to read the absorbance values of uninfected siRNA treated cells and uninfected mock treated cells, without either siRNA or transfection agent. Veritas® software was used to analyze the results. Mock treated samples without transfection agent or siRNA was set at 100% viability.

Construction of Huh7-ISRE-Luc Cells and Assay for siRNA Induction of Interferon-Stimulated Gene Expression.

To investigate possible interferon stimulated gene expression, Huh7 cells were transduced with two recombinant lentiviral vectors, one containing the interferon stimulated response element (ISRE) fused with coding sequence for firefly luciferase (SABiosciences, CLS-008L-1) and the other containing coding sequence for *Renilla* luciferace driven by the CMV promoter/enhancer (SABiosciences CLS-RCL-1). The transduction resulted in a cell line stable for inducible expression of firefly luciferase and constitutive expression of *Renilla* luciferase. The Huh7-ISRE-luc cells were subjected to the indicated treatments using similar reverse transfection and cell culture conditions as described for the antiviral assays described above (in siRNA and cell culture transfections) in a 96-well plate. Firefly and *Renilla* luciferase levels were measured at 8 and 48 hours after plating using the Dual-Glo® luciferase assay reagent (Promega) according to the manufacturer's instructions using the Turner Biosystems plate reader mentioned above. IFN-β at 500 u was used as a positive control for the efficacy of the vectors.

Evaluation of siRNA Antiviral Activity in AG129 Mice.

Strain 129 Sv mice deficient in IFN-α/β and -γ receptors (AG129) were obtained. Mice were 5-6 weeks old at the beginning of the experiments. Mice were allowed food and water ad libitum throughout the studies. Mice were infected intravenously through the tail vein with $10^9$ genomic equivalents (GE) of the DENV-2 strain S221. The $10^9$ GE is equivalent to 20,000 pfu as measured by plaque assay on BHK-21 cells, as performed in Shresta et al, 2006 supra. Additionally, 5 μg of the anti-prM 2H2 monoclonal antibody was administered by intraperitoneal injection on the same day as the infection. (Zellweger R M et al, *Cell Host Microbe* 7, 128-139 (2010), hereby incorporated by reference in its entirety.)

Mice also received a retro-orbital intravenous administration of either PBS or a mixture of Silencer® In Vivo Ready siRNA (Ambion) at a 10 mg/kg dose in Invivofectamine® 2.0 Reagent (Invitrogen) combined as recommended by the manufacturers. (Ambion Product Insert PN 4457174 Rev B, 2010 and Invitrogen Part No: 100010358, revision date 30 Aug. 2010 both of which are incorporated by reference in their entireties). The siRNA or control was added 24 hours before, 24 hours after, and 72 hours after DENV infection. All mice were weighed daily and euthanized when moribund or at the first signs of paralysis. Animals whose weight fell below 80% of weight at the start of the experiment were considered moribund. Mice used in tissue analysis that were collected at 24 hours after infection received siRNA only at 24 hours prior to infection, then were euthanized by isofluorane inhalation at 24 hours post infection. Mice used in tissue analysis that were collected at 72 hours post infection were treated with siRNA 24 hours prior to infection and 24 hours post infection. Blood and tissues harvested as described in Perry S et al, *PLoS Pathol* 7, 31001297 (2011), which is incorporated by reference herein. Quantitative RT-PCR was performed to detect DENV genomes as well as cellular 18S RNA as an internal control as described in Prestwood T R et al, *J Virol* 82, 8411-8421 (2008), which is incorporated by reference herein. Viral load was expressed as GE per ml in serum or GE normalized to copies of 18S rRNA in tissues.

TNF Measurement.

Serum from infected animals was analyzed using a TNF-α ELISA Ready-Set-G0® kit (eBioscience) according to the manufacturer's instructions.

Statistical Analysis.

Cell culture data, viral load data, and serum TNF-α data were analyzed using Student's t-test. For in-vivo data, Kaplan-Meier survival curves were analyzed by log rank test. Error bars represent the standard error of the mean. All statistical analyses were performed with GraphPad Prism® 5 software.

Example 2

Design and Antiviral Activity of Algorithm or Conserved-siRNAs Against Four DENV Serotypes All siRNA used in these examples are defined in Table 1. Two strategies were employed in designing siRNA against DENV genomic sequence. In a first strategy, a predictive algorithm was applied to DENV genomic sequences and two high-scoring potentially effective siRNA sequences were selected for a strain of each of the four Dengue virus serotypes (DENV-1, DENV-2, DENV-3, and DENV-4). The sequences selected through the use of the first strategy were SEQ ID NOs: 2-9. In a second strategy, seven regions that were highly conserved across the GenBank reference sequences for the four serotypes of DENV (SEQ ID NOs: 10-16) and that included at least 19 nucleotides were selected. The sequences derived from the first strategy were not well conserved across all serotypes, with the exception of SEQ ID NO: 5, which was moderately well conserved across the serotypes. None of the siRNA targets obtained through the second strategy (SEQ ID NOs: 10-16) were present in the list of siRNA targets obtained through the first strategy (SEQ ID NOs: 2-9). As a result, a comparison between the two groups in their ability to inhibit different strains of DENV was performed.

Huh7 cells were used to compare the antiviral efficacy of SEQ ID NOs: 2-9 with the antiviral efficacy of SEQ ID NOs: 10-16 because Huh7 cells are easily infected by DENV, easily transfected with siRNA, and are derived from human liver—which has been shown to be infected by DENV in vivo (Jessie K et al, *J Infect Dis* 189, 1411-1418 (2004); Paes, M V et al, *Virology* 338, 236-246 (2005); both of which are incorporated by reference herein.) Growth of each of DENV strains, each representing a different serotype, was monitored in Huh7 cells after transfection with the two strain specific siRNAs (See Example 1 and Table 1) as well as with the conserved SEQ ID NO: 5 and SEQ ID NOs: 10-16. Negative controls included in each experiment comprised an irrelevant negative control siRNA (SEQ ID NO: 1) and a no treatment sample (no siRNA, no transfection reagent).

Huh7 cells were reverse transfected with 100 nM of siRNA two days prior to infection with 0.5 MOI of DENV. The cells were then infected with one of the four DENV serotypes. Two days after infection, the cells were lysed and a Western blot was run using the lysates. Viral envelope glycoprotein (E) and cellular GADPH were detected simultaneously using specific antibodies. GADPH is a housekeeping gene that serves as an internal loading control and as a cell viability indicator. Reduction of infectious viral particle release over time by the siRNAs was monitored with an immunostain-based plaque assay of cell culture supernatants collected at two days post infection. The viruses used in these examples varied with regard in growth characteristics with DENV-2 peak titers an order of magnitude higher than DENV-1, DENV-3, and DENV-4. FIG. 1 shows typical results.

In the experiment shown in FIG. 1, the cell cultures receive a single transfection with 100 nM of each indicated siRNA at 48 hours before infection at an MOI of 0.5. After 2 hours of adsorption, the virus was removed and replaced with a medium that was free of siRNA. At 48 hours post infection, the supernatants were collected for focus forming assays (also called plaque forming assays) and cell lysates were collected for Western blots. Panels A, C, E, and G represent the results from the plaque forming assays and B, D, F, and H represent the results from the Western blots. A sample of uninfected cell lysate is included in the Western blots of DENV 1-3. Each experiment was repeated at least twice with typical results shown. Histograms represent mean values of triplicate assays ±SEM. Asterisks indicate a significant difference relative to the negative control RNA (SEQ ID NO: 1) treated group. Significance is defined as a P<0.05 by Student's t-test.

With the exception of SEQ ID NO: 9, all of the siRNA in the serotype-siRNA group consisting of SEQ ID NOs: 2-9 markedly suppressed virus protein production and infectious virus produced and therefore served as benchmarks to evaluate the efficacy of the conserved-siRNA group consisting of SEQ ID NOs: 10-16. SEQ ID NOs: 14 and 15 were generally ineffective. Note that SEQ ID NO: 15 includes the DENV 3' CS sequence (CAGCAUAUUG) a highly conserved motif in mosquito borne flaviviruses (Hahn C S et al, *J Mol Biol* 198, 33-41 (1987); Khromykh A A et al, *J Virol* 75, 6719-6728 (2001); Markoff L, *Adv Virus Res* 59, 177-228 (2003); Villordo S M and Gamarnik A V, *RNA* 16, 2325-2335 (2011); You S and Padmanabhan R, *J Biol Chem* 274, 33714-33722 (1999), all of which are incorporated by reference herein). SEQ ID NO: 13 showed some activity against DENV-3 and DENV-4 while SEQ ID NO: 16 had some activity against DENV-2 and DENV-3. SEQ ID NO: 5 was active not only against DENV-2 (against which it was predicted to be active as part of the serotype siRNA group) but also against DENV-3 and DENV-4. With regard to the particular strains selected to represent each serotype, SEQ ID NO: 5 has no mismatches with DENV-2, one mismatch with DENV-4, two mismatches with DENV-3, and three mismatches with DENV-1 (See Table 4).

TABLE 4

Number of mismatches between conserved-siRNA and SEQ ID NOs: 5, 10-16.

| | siRNA SEQ ID NO: | | | | | | | |
|---|---|---|---|---|---|---|---|---|
| Virus (strain | 10 | 11 | 12 | 13 | 14 | 15 | 16 | 5 |
| DENV1 (West-Pac*) | 0 | 0 | 1 | 0 | 0 | 0 | 0 | 3 |
| DENV2 (NGC*) | 0 | 0 | 0 | 0 | 0 | 0 | 0 | 0 |
| DENV2 (S210*) | 0 | 0 | 0 | 0 | 0 | 0 | 0 | 0 |
| DENV3 (H87*) | 0 | 0 | 1 | 0 | 1 | 0 | 0 | 2 |
| DENV4 (H241*) | N/A# | 2 | 0 | 0 | 0 | 0 | 0 | 1 |
| DENV1 (Ref Seq^) | 0 | 0 | 1 | 0 | 0 | 0 | 0 | 3 |
| DENV2 (Ref Seq^) | 0 | 0 | 0 | 0 | 0 | 0 | 0 | 0 |
| DENV3 (Ref Seq^) | 0 | 0 | 2 | 0 | 0 | 0 | 0 | 2 |
| DENV4 (Ref Seq^) | 2 | 1 | 0 | 0 | 0 | 0 | 0 | 0 |

*strain of DENV used in these examples (See Example 1)
^GenBank Reference Sequence- see footnote 1 in Table 1.
The 5' terminal nucleotides of this GenBank entry may be inaccurate.

The most consistent results against all strains were seen with SEQ ID NO: 10 and SEQ ID NO: 12. SEQ ID NO: 10 has no mismatches with the strains of DENV-1, DENV-2, and DENV-3 used herein. Agreement with DENV-4 is uncertain due to questions regarding the accuracy of the GenBank sequence annotation at the H241 5'-terminal region. SEQ ID NO: 12 suppressed the titers of all four strains robustly—by more than 98% compared to control siRNA (See FIG. 1). SEQ ID NO: 12 has perfect agreement with the DENV-2 and DENV-4 strains used herein and one mismatched base with the DENV-1 and DENV-3 strains used herein, with similar results to the reference sequences (See Table 4). This surprising result demonstrates that siRNA designed solely on the basis of conservation across GenBank reference sequences were active against randomly selected representative strains from each of the four serotypes.

Example 3

Ruling Out Cytotoxicity as a Mechanism of Action of the siRNA

One possible interpretation of these results would be that the siRNA used herein were toxic to the Huh7 cells and killed the cells before virus could be made. To rule out this possibility, Huh7 cells were transfected with 100 nM of irrelevant negative control siRNA (SEQ ID NO: 1), SEQ ID NO: 10, SEQ ID NO: 12, SEQ ID NO: 5, an siRNA specific for West Nile virus (SEQ ID NO: 17), and an siRNA specific for yellow fever virus (SEQ ID NO: 18). These siRNA were transfected into Huh7 cells under the same conditions as described in Example 2 and incubated for 48 hours. Cell viability was measured on the basis of ATP utilization. No significant differences in viability were seen using any siRNA combined with the 1:400 dilution of RNAiMAX used in this example. This shows that cytotoxicity of the siRNAs on Huh7 cells is ruled out as the reason for the inhibition of virus production.

Example 4

Alignment of Conserved-siRNA Against all DENV Sequences Present in GenBank

Figures 2A, 2B:
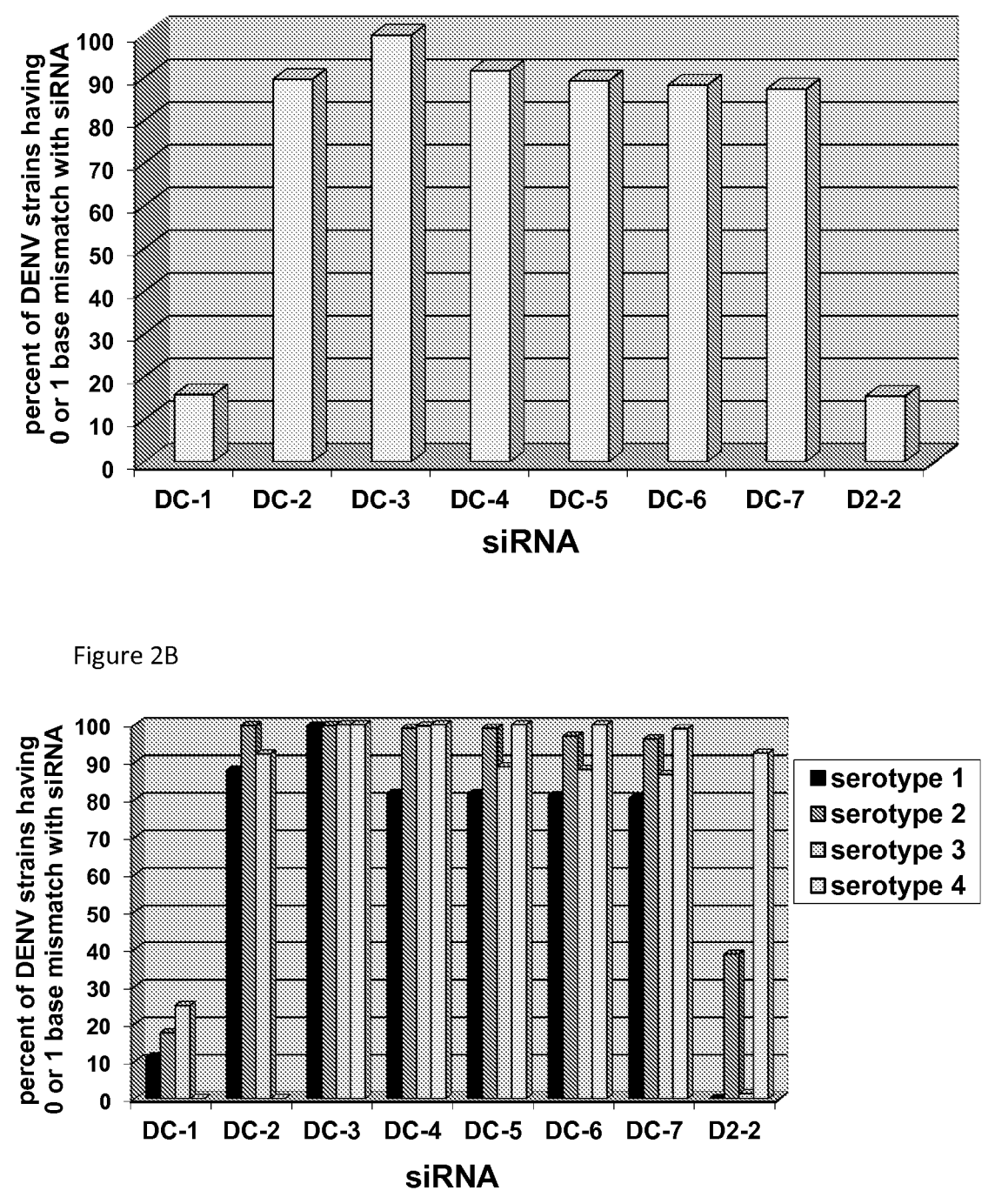

Full-length sequences of 2754 individual isolates of DENV encompassing all four serotypes were aligned. The percentage of sequences that had a 0 or 1 base difference from SEQ ID NOs: 5 and 10-16 was then determined. SEQ ID NOs: 11 and 13-16 were conserved at between 86% and 92%. SEQ ID NOs: 10 and 5 were each conserved in 15-16% of the GenBank sequences (see FIG. 2A). SEQ ID NO: 12 was conserved in over 99% of all DENV sequences analyzed. A similar distribution was seen when the full-length sequences were subdivided into individual serotypes. While each of SEQ ID NOs: 10-11 and 13-16 had lower conservation across at least one of the four serotypes, SEQ ID NO: 12 was highly conserved across all four serotypes (See FIG. 2B). FIG. 2 is a graphical depiction of the conservation of SEQ ID NOs: 5 and 10-16. FIG. 2A shows the total number of best alignments with an exact match or one mismatch divided by the total number of DENV virus sequences in GenBank. FIG. 2B shows the total number of best alignments having an exact match or one mismatch in each serotype divided by the number of strains in each serotype (See Example 1). SEQ ID NO: 12 is the first siRNA conserved across all four Dengue serotypes that is also shown to be highly active in preventing Dengue virus infection across all four serotypes.

Example 5

SEQ ID NO: 12 Inhibits Multiple Rounds of DENV Infection

In FIG. 3, Huh7 cells were transfected with SEQ ID NO: 12 siRNA 48 hours prior to infection with each serotype at an input MOI of 0.2. After a two-hour adsorption period, the virus was removed and replaced with medium containing no siRNA. Supernatants were collected daily for five days following the infection. Error bars indicate the standard error of the mean of triplicate plaque assays. Recovery of DENV-1, DENV-3, and DENV-4 steadily increased over a period of five days—a result consistent with several rounds of infection. At each time point, SEQ ID NO: 12 transfected cultures showed 90-99% lower viral recovery relative to controls transfected with the SEQ ID NO: 1 negative control siRNA. SEQ ID NO: 12 thus delayed the accumulation of extracellular virus by 1-2 days for up to five days post infection—a full week after the single transfection. The DENV-2 strain used grew more quickly and to a higher titer, resulting in cell death beginning at day 3 following the infection. That said, cells transfected with SEQ ID NO: 12 still showed less viral accumulation at days 1 and 2 following the infection relative to controls transfected with SEQ ID NO: 1.

Example 6

Figure 1C:
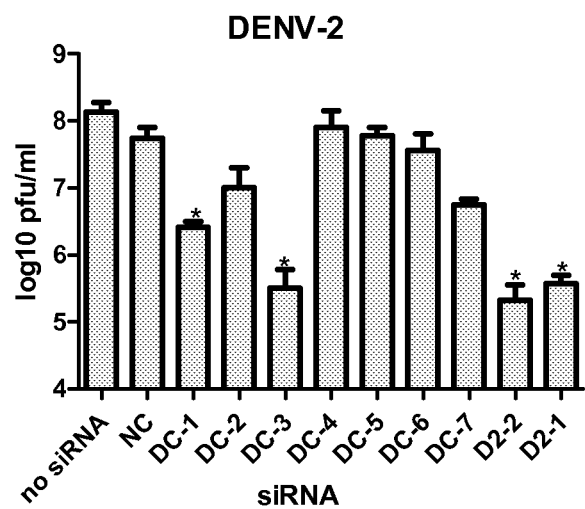
Figure 1D:
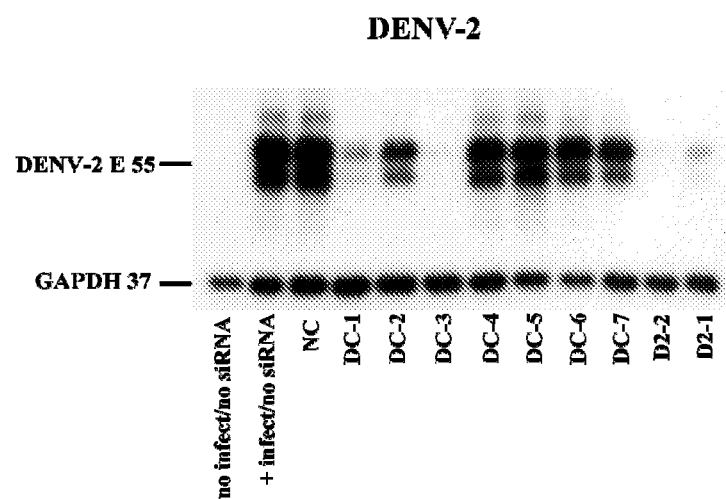
Figure 1E:
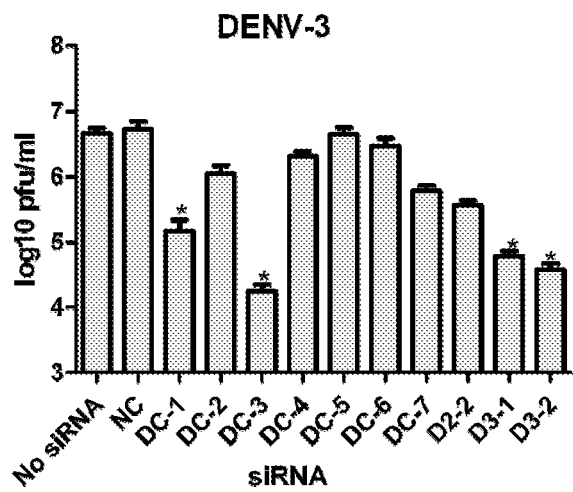
Figure 1F:
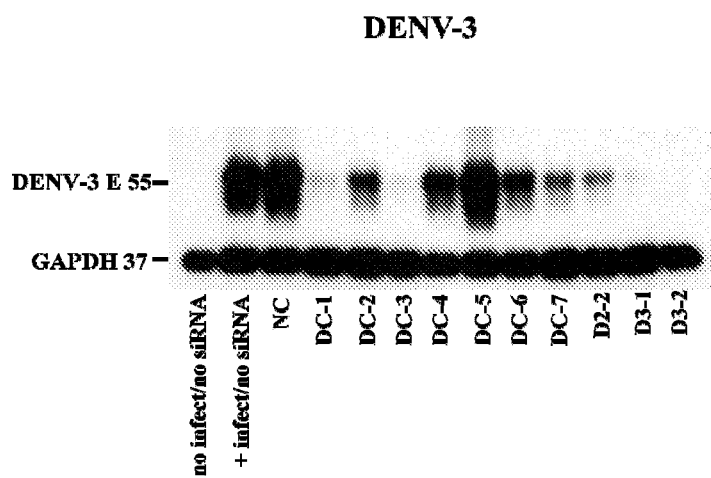
Figure 1G:
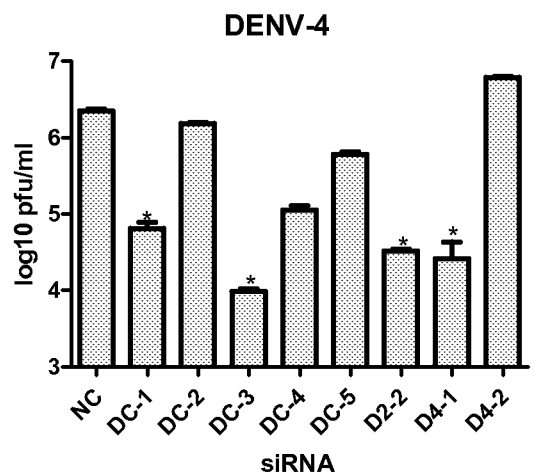
Figure 1H:
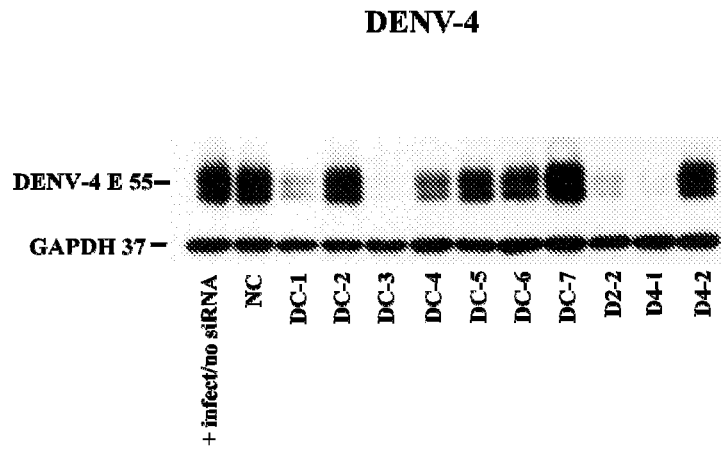
Figure 3A:
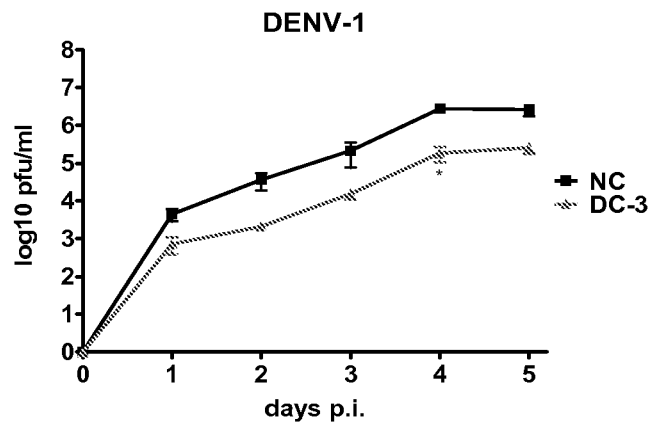
Figure 3B:
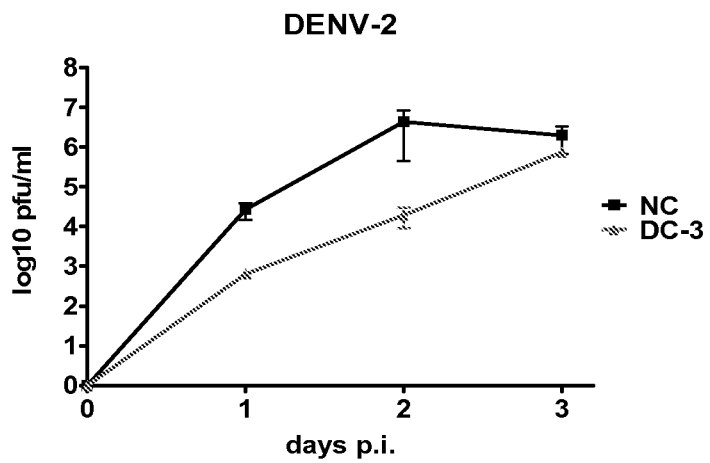
Figure 3C:
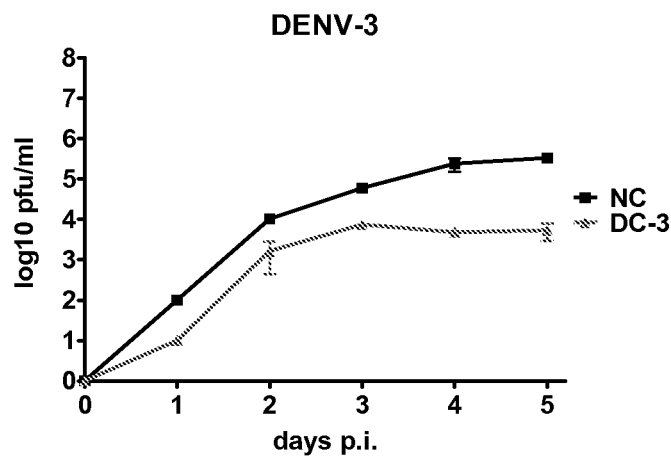
Figure 3D:
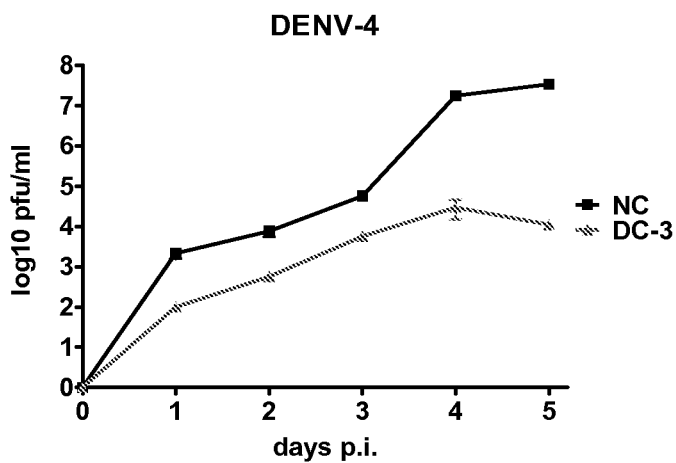
Figure 4A:
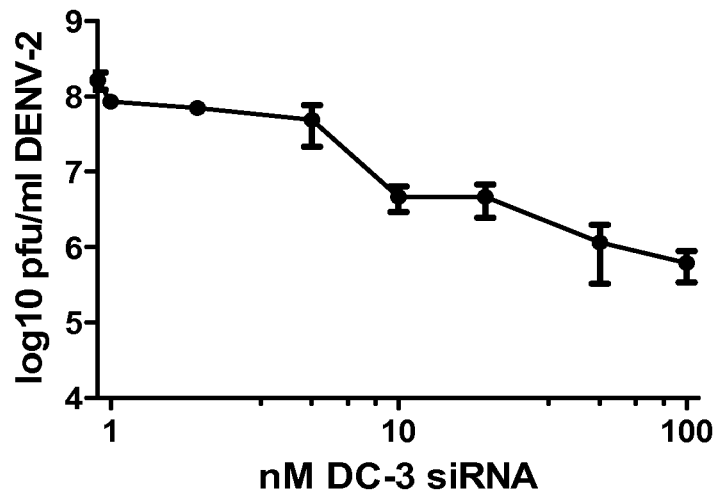
Figure 4B:
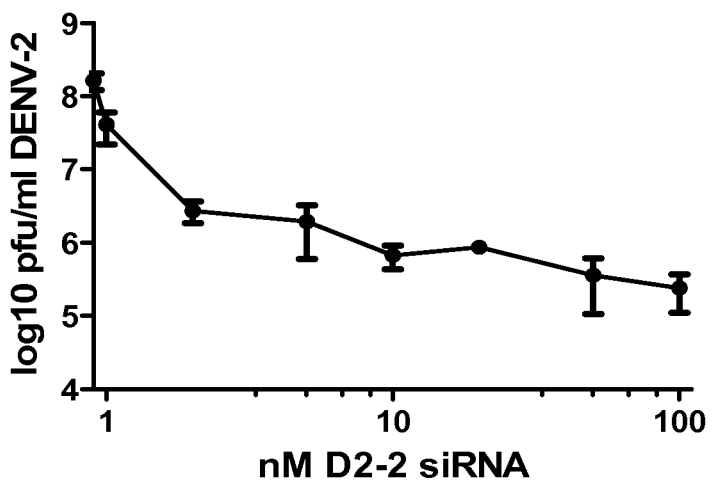

Comparison of the Inhibitory Concentrations of the Serotype-siRNA Group (SEQ ID NOs: 2-9) Versus the Conserved-siRNA Group (SEQ ID NOs: 10-16) Against Dengue Infection The conserved-siRNA SEQ ID NO: 12 and the serotype-siRNA SEQ ID NO: 5 each reduced DENV-2 virus production by more than two orders of magnitude (logs) at a concentration of 100 nM (see FIG. 1C). These two siRNAs were then compared in a dose-response experiment against the DENV-2 strain—the strain that replicated most robustly of those tested. In FIG. 4, Huh7 cell cultures were transfected once with the indicated concentration of SEQ ID NO: 12 and SEQ ID NO: 5 siRNA 48 hours prior to infection with DENV-2 at an MOI of 0.5. After a two-hour adsorption, the virus was removed and replaced with medium containing no siRNA. At 48 hours post infection, supernatants were collected. Each experiment was carried out at least twice. Similar results were seen with each experiment and representative results are shown. The bars show mean values of triplicate plaque assays ±SEM. As seen in FIG. 4, viral release was suppressed by more than ten-fold when SEQ ID NO: 5 was present at under 2 nM. This results in an $IC_{90}$ of 1.4 nM. $IC_{90}$ is the concentration of drug producing a 90% reduction in the amount of virus produced compared to mock-treated cells. SEQ ID NO: 12 was less potent with an $IC_{90}$ of 9.8 nM, but surprisingly comparable since SEQ ID NO: 5 was selected as a specific inhibitor of DENV-2. Notably, both siRNAs caused a viral titer more than 100-fold lower than the control at a concentration of 50 nM.

Example 7

SEQ ID NO: 12 Inhibits DENV-2 Infection and Disease in AG129 Mice

Figure 6A:
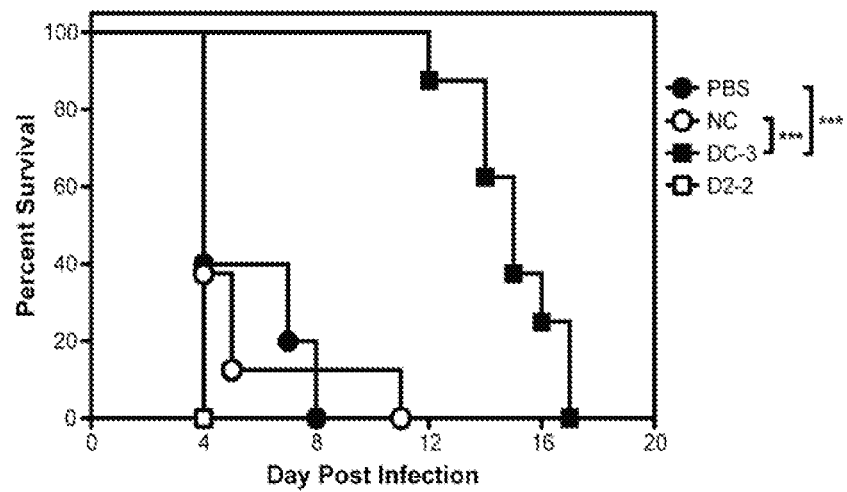
Figure 6B:
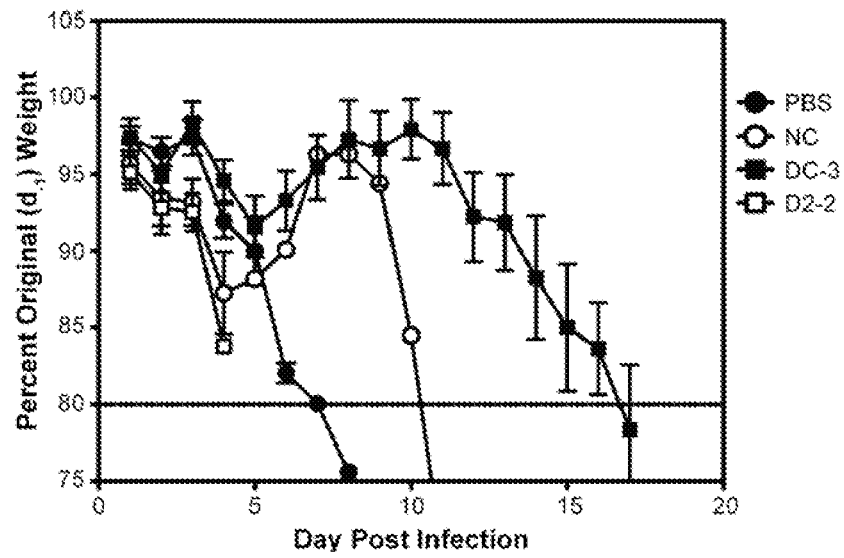
Figure 6C:
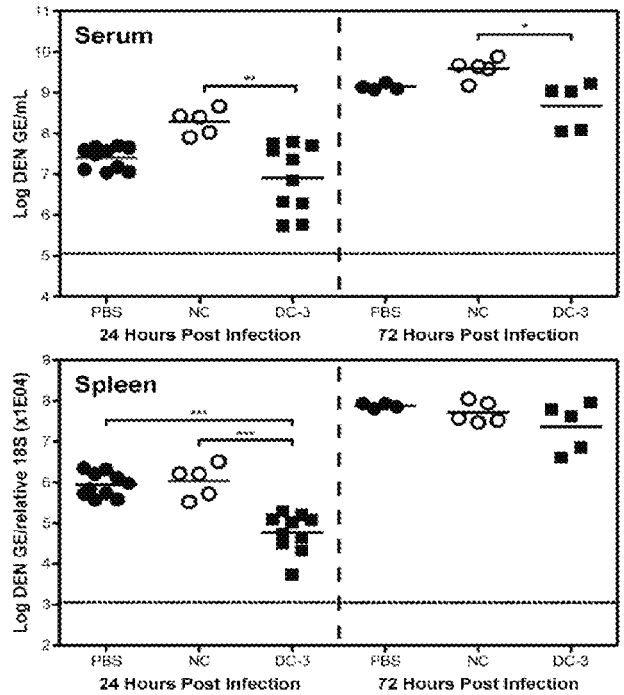
Figure 6D:
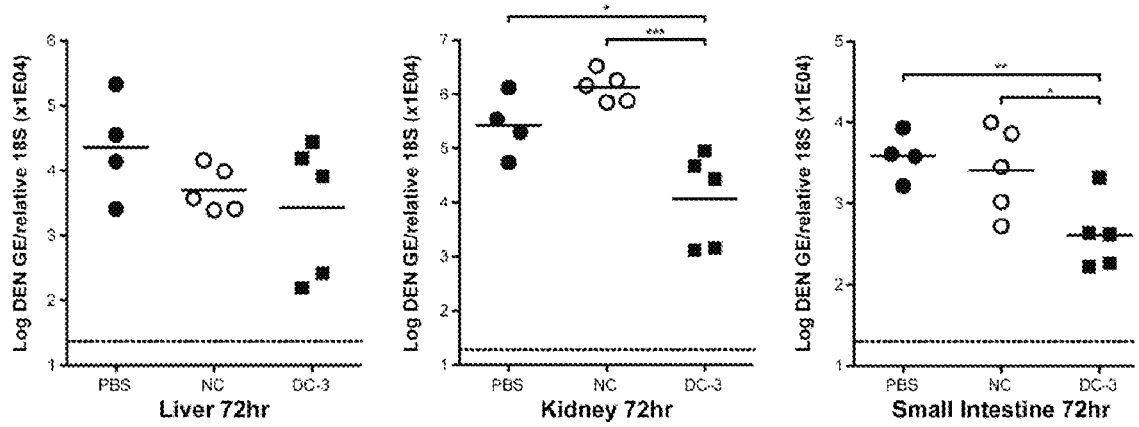
Figure 6E:
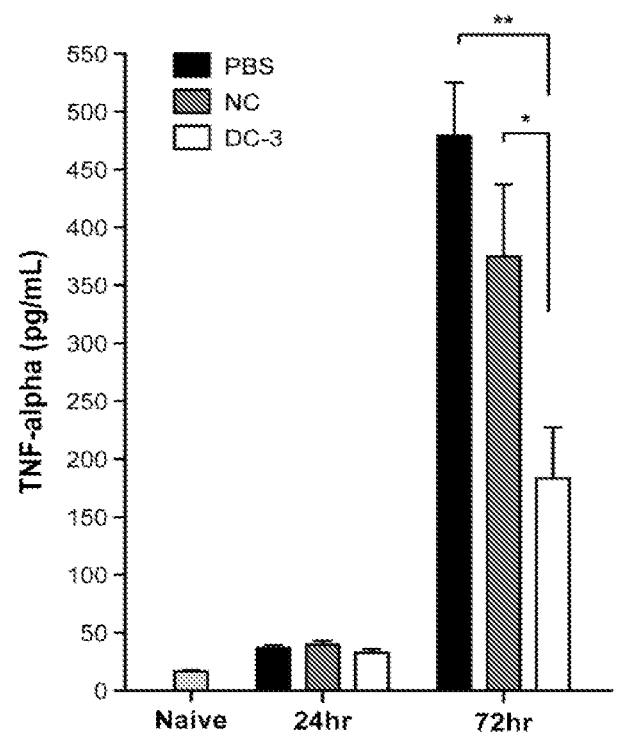

AG129 mice were infected with the DENV-2 strain S221 in the presence of the anti-Dengue virus prM monoclonal antibody 2H2. Infection with DENV-2 in combination with 2H2 mediates severe pathology and death between days 4-8 (Zellweger R M et al, 2010 supra). The mice were treated with 10 mg/kg of the indicated siRNA via a retro-orbital intravenous injection at 24 hours before, 24 hours after, and 72 hours after tail vein administration of $10^9$ genomic equivalents of DENV-2 and intraperitoneal injection of 5 μg of 2H2. FIG. 6A shows the survival time of the mice. Five mice made up the PBS group (no siRNA). Eight mice made up the negative control (NC) group (given SEQ ID NO: 1 negative control siRNA). Eight mice made up the DC-3 group (given SEQ ID NO: 12 siRNA). Five mice made up the D2-2 group (given SEQ ID NO: 5 siRNA). The survival curve shows the combined results of two separate survival experiments carried out under similar conditions at different times. The difference between SEQ ID NO: 12 treated and all other groups is statistically significant by log-rank analysis (P<0.0001). FIG. 6B shows the changes in body weight of the four groups of mice over time. Body weight was measured daily and presented as a percentage of animal weight 24 hours prior to infection. FIG. 6C shows the viral load in serum and spleen at 24 hours post infection and 72 hours post infection. For the serum and spleen collected 24 hours post infection, ten mice made up the PBS (no siRNA) group, five mice made up the NC group (given SEQ ID NO: 1), and ten mice made up the DC-3 group (given SEQ ID NO: 12 siRNA). For all tissues collected at 72 hours post infection, there were five mice per group. FIG. 6D shows the viral load in liver, kidney, and small intestine at 72 hours post infection. In both FIGS. 6C and 6D, viral load was quantified by RT-PCR as described in Example 1. * indicates P<0.0005,  indicates P<0.005, * indicates P<0.05 by Student's t-test. FIG. 6E indicates the expression of TNF-α in serum collected from uninfected and infected mice at 24 hours and at 72 hours post infection (n=5 mice per group.) TNF-α was detected by ELISA as described in Example 1. ** indicates P<0.005 and * indicates P<0.05 by Student's t test.

Modified siRNAs of the sequences listed above and a specialized transfection agent were administered in vivo (See Example 1). Survival of mice treated with SEQ ID NO: 12 was significantly extended to a median survival time of 14 days as compared to 5 days for the negative controls (See FIG. 6A). SEQ ID NO: 5 had no effect on the survival of the infected mice as compared to the negative controls. Seventeen of the eighteen animals treated with SEQ ID NO: 5 or the negative controls succumbed to an early death phenotype, indicated by hunched posture, ruffled fur, and severe weight loss within the first eight days post infection. In contrast, the eight SEQ ID NO: 12 treated mice maintained normal appearance and behavior until at least eleven days post infection and were euthanized between twelve and seventeen days post infection following signs of hind-limb paralysis. Body weight measurements reflected disease severity with SEQ ID NO: 12 treated mice retaining on average 95% of their pre-infection body weight for at least eleven days post infection.

Viral load in animals was assessed by RT-PCR in a number of tissues. In the animal model of infection used in this example, initial viral infection occurs in the spleen with viral load increasing in other tissues throughout the several days following infection. By 24 hours post infection, mice treated with SEQ ID NO: 12 siRNA had an 18-fold lower viral load in the spleen than either negative control group (See FIG. 6C). Mice treated with SEQ ID NO: 12 also showed a significantly lower level of viremia compared to the mice treated with the SEQ ID NO: 1 negative control siRNA (but not the PBS treated negative control.) In serum and spleen collected 72 hours post infection, viral load was higher in all treatment groups when compared to serum and spleen collected 24 hours post infection. At 72 hours, viremia in mice treated with SEQ ID NO: 12 was 8 fold lower than mice treated with the SEQ ID NO: 1 negative control siRNA and remained 3 fold lower than the PBS treated negative control. The largest effect of treatment with SEQ ID NO: 12 was observed in the kidney where viral load was 23 fold lower than the PBS treated controls and where viral load was 117 fold lower compared to the SEQ ID NO: 1 treated controls.

Tumor necrosis factor alpha is a key mediator of severe DENV disease in the mouse model used in this example (See Zellweger et al, 2010, supra). Serum collected at 72 hours post infection showed that PBS treated and SEQ ID NO: 1 treated negative control mice had significantly higher serum TNF-α than mice treated with SEQ ID NO: 12 (See FIG. 6E). This indicates that treatment with SEQ ID NO: 12 causes not just increased survival, better maintenance of body weight, and improved qualitative measures of survival, but also causes inhibition of a cytokine known to mediate the early death phenotype in this animal model.

Example 8 siRNA Targeting the 5'CS Inhibit WNV and YFV

The 5' region of all mosquito-borne flaviviruses shares eight nucleotides of sequence. However, the adjacent sequence varies between viral species. Species-specific siRNA was designed to target the 5' CS region of West Nile virus and yellow fever virus. SEQ ID NOs: 17 and 18 target the eleven nucleotide 5' CS region and the adjacent eight nucleotides in the 3' direction. SEQ ID NO: 17 was 100% conserved across all 284 complete genomes against which it was tested by comparative alignment. SEQ ID NO: 17 shares similarity with SEQ ID NO: 12, with twelve bases complementary to SEQ ID NO: 12 present in WNV and seventeen bases targeted by SEQ ID NO: 17 present in DENV-2 (See FIG. 5A). Up to eighteen nucleotides in a sequence of nineteen contiguous nucleotides are predicted to comprise the 5' CS region of YFV (Villordo S M and Gamarnik A V, 2009 supra. All 18 YFV genomes analyzed had 100% conservation with SEQ ID NO: 18.

FIG. 5 indicates the comparison of genomic sequences and siRNA targets in DENV2 and WNV at the 5' CS region and the dose-response efficacy of siRNA targeting the 5' CS region of WNV or YFV in Huh7 cell cultures. FIG. 5A shows the alignment of the 5' CS regions of DENV-2 bases 131-158 (top) and WNV bases 136-161. The 5' CS of each virus is indicated in bold. The targets of SEQ ID NO: 12 and SEQ ID NO: 17 are underlined. Common sequence between DENV-2 and WNV is shaded. FIG. 5B shows cells that received a single transfection of the indicated siRNA at 48 hours prior to infection with WNV at an MOI of 0.5. After a 2 hour adsorption period, the virus was removed and replaced with medium containing no siRNA. At 24 hours post infection, supernatants were collected for plaque assays. FIG. 5C shows cells that received a single transfection of the indicated siRNA at 48 hours prior to infection with YFV at an MOI of 0.5. After a 2 hour adsorption period, the virus was removed and replaced with medium containing no siRNA. At 72 hours post infection, supernatants were collected for plaque assays. In both graphs the histograms show the mean values of triplicate plaque assays ±SEM. Asterisks indicate significant differences relative to the group treated with the SEQ ID NO: 1 negative control siRNA. * indicates P<0.05 by Student's t-test.

Transfection with SEQ ID NO: 17 caused 5-fold less viral titer at 50 nM and 20 fold less viral titer at 100 nM than negative controls (See FIG. 5B). Transfection with SEQ ID NO: 18 caused a viral titer that was orders of magnitude lower than negative controls even at low nanomolar concentrations (See FIG. 5C). Specificity of SEQ ID NO: 17 and SEQ ID NO: 18 were tested further. Huh7 cells were transfected with 100 nM of SEQ ID NO: 1 (negative control); SEQ ID NO: 17, and SEQ ID NO: 18, then infected with 0.5 MOI DENV-2 under the conditions specified in Example 1 and Example 2. Transfection with SEQ ID NO: 17 led to the production of 3-fold to 4-fold less DENV-2 than the negative control. Transfection with SEQ ID NO: 18 had a negligible effect on viral titer relative to the negative control.

Example 9

Anti-Flaviviral siRNA do not Induce Interferon Stimulated Gene Expression

It has been reported that siRNA can produce innate immune stimulation in a sequence-specific manner (Judge A D et al, *Nat Biotechnol* 23, 457-462 (2005) incorporated by reference herein.) As a result, treatment with siRNA has been shown to stimulate the production of interferons by cells. Interferons are potent antiviral compounds. Therefore it would be possible that the siRNA were not affecting viral titer by specific binding to their target sequences, but rather by non-specific induction of interferon expression. To explore this possibility, siRNA comprising SEQ ID NO: 1, SEQ ID NO: 12, SEQ ID NO: 17, and SEQ ID NO: 18 were transfected at 100 nM into Huh7-ISRE-luc cells which contain a stably integrated interferon stimulated response element (ISRE) fused to a luciferase coding sequence under the conditions detailed in Example 1 and Example 2. None of the siRNA tested caused a significant stimulation of interferon when measured at 8 hours or 48 hours after infection. The β-interferon positive control induced a high level of reporter signal.

What is claimed is:

1. A pharmaceutical composition comprising:
a therapeutically effective amount of an siRNA comprising a first nucleic acid, the first nucleic acid comprising a polyribonucleic acid sequence selected from the group consisting of SEQ ID NO: 12 and SEQ ID NO: 19.

2. The pharmaceutical composition of claim 1, wherein the first nucleic acid comprises a polyribonucleic acid of SEQ ID NO: 12 and wherein the siRNA further comprises a second nucleic acid, wherein the second nucleic acid comprises a polyribonucleic acid of SEQ ID NO: 19 and wherein the first nucleic acid and the second nucleic acid form a nucleotide duplex.

3. The pharmaceutical composition of claim 2 wherein the first nucleic acid and the second nucleic acid are linked to one another by a first linker to form a hairpin secondary structure.

4. The pharmaceutical composition of claim 3 wherein the first nucleic acid and the second nucleic acid are linked to one another by a second linker to form a circular single-stranded polynucleotide.

5. The pharmaceutical composition of claim 1 wherein the first nucleic acid is less than or equal to 27 nucleotides in length.

6. The pharmaceutical composition of claim 5 wherein the first nucleic acid comprises a 5' overhang and wherein the 5' overhang is 1-4 nucleotides in length.

7. The pharmaceutical composition of claim 5 wherein the first nucleic acid comprises a 3' overhang and wherein the 3' overhang is 1-4 nucleotides in length.

8. The pharmaceutical composition of claim 1 wherein the first nucleic acid comprises a modified nucleotide.

9. The pharmaceutical composition of claim 8 wherein the modified nucleotide comprises a ribonucleotide comprising a moiety selected from the group consisting of 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl.

10. The pharmaceutical composition of claim 8 wherein the modified nucleotide comprises a locked nucleic acid nucleotide.

11. The pharmaceutical composition of claim 10 wherein the locked nucleic acid nucleotide is selected from the group consisting of 2'-O, 4'-C-methylene-(D-ribofuranosyl)nucleotide, 2'-O-(2-methoxyethyl) (MOE) nucleotide, 2'-methylthio-ethyl nucleotide, 2'-deoxy-2'-fluoro (2'F) nucleotide, 2'-deoxy-2'-chloro (2Cl) nucleotide, and 2'-azido nucleotide.

12. The pharmaceutical composition of claim 8 wherein the modified nucleotide comprises a G-clamp nucleotide.

13. The pharmaceutical composition of claim 8 wherein the modified nucleotide comprises a nucleotide base analog.

14. The pharmaceutical composition of claim 13 wherein the nucleotide base analog comprises a moiety selected from the list consisting of C-phenyl, C-naphthyl, inosine, azole carboxamide, and nitroazole derivative.

15. The pharmaceutical composition of claim 14 wherein the group is a nitroazole derivative and wherein the nitroazole derivative is a moiety selected from the group consisting of 3-nitropyrrole, 4-nitroindole, 5-nitroindole, and 6-nitroindole.

16. The pharmaceutical composition of claim 1 wherein the first nucleic acid comprises a terminal cap moiety.

17. The pharmaceutical composition of claim 16 wherein the terminal cap moiety is of a class selected from the group consisting of inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3 aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, bridging methylphosphonate, non-bridging methylphosphonate and 5'-mercapto moieties.

18. The pharmaceutical composition of claim 1 wherein the first nucleic acid comprises a phosphate backbone modification.

19. The pharmaceutical composition of claim 18 wherein the phosphate backbone modification is a substitution selected from the list consisting of phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions.

20. The pharmaceutical composition of claim 1 further comprising a conjugate attached to the first nucleic acid.

21. The pharmaceutical composition of claim 20 wherein the conjugate is attached to the 5'-end of the first nucleic acid.

22. The pharmaceutical composition of claim 20 wherein the conjugate is attached to the 3'-end of the first nucleic acid.

23. The pharmaceutical composition of claim 1 wherein the siRNA is provided as naked siRNA.

24. The pharmaceutical composition of claim 1 further comprising a pharmaceutically acceptable carrier.

25. The pharmaceutical composition of claim 24 wherein the pharmaceutically acceptable carrier comprises a system selected from the group consisting of a lipid based carrier system, a polymer based carrier system, a cyclodextrin based carrier system, a protein based carrier system.

26. The pharmaceutical composition of claim 25 wherein the system comprises a lipid based carrier system wherein the lipid based carrier system comprises a component selected from the group consisting of a stabilized nucleic acid-lipid particle, a cationic lipid, a liposome nucleic acid complex, a liposome, a micelle, and a virosome.

27. A method of treating a disease resulting from dengue virus infection in a subject, the method comprising:
    administering a therapeutically effective amount of the pharmaceutical composition of claim 1 to the subject.

28. The method of claim 27 wherein the subject is human.

29. The method of claim 27 wherein the subject displays symptoms or signs of a disease resulting from dengue virus infection and wherein the pharmaceutical composition is administered therapeutically.

30. The method of claim 27 wherein the subject displays no symptoms or signs of disease resulting from dengue virus infection but is or will be in a region in which dengue virus is endemic and wherein the pharmaceutical composition is administered prophylactically.

31. The method of claim 27 wherein the subject displays symptoms or signs of dengue disease and wherein the dengue virus serotype is unknown.

32. The method of claim 27 wherein the route of administration is selected from the group consisting of injection, oral, sublingual, rectal, transdermal, intranasal, vaginal, retro-orbital, and inhalation.

33. The method of claim 32 wherein the route of administration is injection and wherein the mode of injection is selected from the group consisting of subcutaneous, intramuscular, intradermal, intraperitoneal, and intravenous.

* * * * *